(12) United States Patent
Medoff et al.

(10) Patent No.: US 10,510,510 B2
(45) Date of Patent: Dec. 17, 2019

(54) TREATING BIOMASS

(71) Applicant: XYLECO, INC., Wakefield, MA (US)

(72) Inventors: Marshall Medoff, Brookline, MA (US); Anthony Peters, Fremont, CA (US); Thomas Craig Masterman, Rockport, MA (US); Robert Paradis, Burlington, MA (US); Kenny Kin-Chui Ip, Fremont, CA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

(21) Appl. No.: 15/487,312

(22) Filed: Apr. 13, 2017

(65) Prior Publication Data

US 2017/0221679 A1 Aug. 3, 2017

Related U.S. Application Data

(63) Continuation of application No. 14/434,682, filed as application No. PCT/US2013/064322 on Oct. 10, 2013, now Pat. No. 9,659,748.

(Continued)

(51) Int. Cl.
*H01J 37/317* (2006.01)
*B01J 19/08* (2006.01)
(Continued)

(52) U.S. Cl.
CPC ......... *H01J 37/317* (2013.01); *B01J 19/085* (2013.01); *C10L 1/02* (2013.01); *C12P 19/02* (2013.01);

(Continued)

(58) Field of Classification Search
CPC ............... H01J 37/317; H01J 2237/202; H01J 2237/3165; H01J 33/04; H01J 5/18;
(Continued)

(56) References Cited

U.S. PATENT DOCUMENTS 2,674,381 A 4/1954 Cady
2,993,120 A 7/1961 Emannelson
(Continued)

FOREIGN PATENT DOCUMENTS

CN 202670653 U 1/2013
EP 0458162 A1 11/1991
(Continued)

OTHER PUBLICATIONS

Alfenore, S., et al. "Improving ethanol production and viability of *Saccharomyces cerevisiae* by a vitamin feeding strategy during fed-batch process," Applied Microbiology and Biotechnology, vol. 60, No. 1, pp. 67-72 (Oct. 2002).

(Continued)

*Primary Examiner* — Xiuyu Tai
(74) *Attorney, Agent, or Firm* — Leber IP Law; Narendra K. Vaish

(57) ABSTRACT

Methods and systems are described for processing cellulosic and lignocellulosic materials and useful intermediates and products, such as energy and fuels. For example, irradiating methods and systems are described to aid in the processing of the cellulosic and lignocellulosic materials. The electron beam accelerator has multiple windows foils and these foils are cooled with cooling gas. In one configuration a secondary foil is integral to the electron beam accelerator and in another configuration the secondary foil is part of the enclosure for the biomass conveying system.

45 Claims, 7 Drawing Sheets

Related U.S. Application Data

(60) Provisional application No. 61/711,801, filed on Oct. 10, 2012, provisional application No. 61/711,807, filed on Oct. 10, 2012.

(51) Int. Cl.

| | | |
|---|---|---|
| *C12P 19/02* | (2006.01) | |
| *C12P 19/14* | (2006.01) | |
| *H01J 5/18* | (2006.01) | |
| *C10L 1/02* | (2006.01) | |
| *H01J 7/26* | (2006.01) | |
| *H01J 33/04* | (2006.01) | |
| *G21K 5/04* | (2006.01) | |
| *G21K 5/10* | (2006.01) | |

(52) U.S. Cl.
CPC .............. *C12P 19/14* (2013.01); *H01J 5/18* (2013.01); *H01J 7/26* (2013.01); *H01J 33/04* (2013.01); *B01J 2219/0871* (2013.01); *B01J 2219/0879* (2013.01); *C10L 2200/0469* (2013.01); *C10L 2290/36* (2013.01); *C12P 2201/00* (2013.01); *G21K 5/04* (2013.01); *G21K 5/10* (2013.01); *H01J 2237/202* (2013.01); *H01J 2237/3165* (2013.01)

(58) Field of Classification Search
CPC .... H01J 7/26; B01J 19/085; B01J 2219/0871; B01J 2219/0879; C10L 1/02; C10L 2200/0469; C10L 2290/36; C12P 19/02; C12P 19/14; C12P 2201/00; G21K 5/04; G21K 5/10; A23L 3/263; F27B 9/066; F27B 9/045; F27D 99/0075; G21F 3/00; G21F 1/08

See application file for complete search history.

(56) References Cited

U.S. PATENT DOCUMENTS

| | | | |
|---|---|---|---|
| 3,676,673 A * | 7/1972 | Coleman | F27B 9/066 250/398 |
| 3,844,890 A | 10/1974 | Horikoshi et al. | |
| 3,934,144 A | 1/1976 | Green et al. | |
| 3,939,286 A | 2/1976 | Jelks | |
| 4,243,750 A | 1/1981 | Muller et al. | |
| 4,261,905 A | 4/1981 | Preobrazhenskaya et al. | |
| 4,268,505 A | 5/1981 | Yoshikumi et al. | |
| 4,274,163 A | 6/1981 | Malcom et al. | |
| 4,275,163 A | 6/1981 | Gallo | |
| 4,303,649 A | 12/1981 | Jones | |
| 4,305,000 A | 12/1981 | Cheever | |
| 4,321,328 A | 3/1982 | Hoge | |
| 4,337,152 A | 6/1982 | Lynch | |
| 4,387,476 A | 6/1983 | Bueb et al. | |
| 4,435,307 A | 3/1984 | Barbesgaard et al. | |
| 4,482,046 A | 11/1984 | Kraus | |
| 4,760,264 A | 7/1988 | Barrett | |
| 4,769,082 A | 9/1988 | Kumakura et al. | |
| 4,813,532 A | 3/1989 | Harper | |
| 5,055,204 A | 10/1991 | Bogart | |
| RE33,935 E | 5/1992 | Fujimoto et al. | |
| 5,122,598 A | 6/1992 | della Valle et al. | |
| 5,131,525 A | 7/1992 | Musschoot | |
| 5,181,715 A | 1/1993 | Ohkoda et al. | |
| 5,314,978 A | 5/1994 | Kim et al. | |
| 5,392,529 A | 2/1995 | Bailey et al. | |
| 5,396,074 A | 3/1995 | Peck et al. | |
| 5,401,973 A | 3/1995 | McKeown et al. | |
| 5,462,155 A | 10/1995 | Demar et al. | |
| 5,530,255 A | 6/1996 | Lyons et al. | |
| 5,538,730 A | 7/1996 | Romeo et al. | |
| 5,593,890 A | 1/1997 | Flores-Cotera et al. | |
| 5,621,270 A | 4/1997 | Allen | |
| 5,635,714 A | 6/1997 | Nablo et al. | |
| 5,661,305 A | 8/1997 | Lawrence et al. | |
| 5,753,474 A | 5/1998 | Ramey | |
| 5,876,505 A | 3/1999 | Klyosov et al. | |
| 5,877,582 A | 3/1999 | Nishimura | |
| 5,882,737 A | 3/1999 | Eckhoff | |
| 5,916,780 A | 6/1999 | Foody et al. | |
| 5,916,929 A | 6/1999 | Knobel et al. | |
| 5,994,706 A | 11/1999 | Allen et al. | |
| 6,011,008 A | 1/2000 | Domb et al. | |
| 6,127,687 A | 10/2000 | Williams et al. | |
| 6,220,427 B1 | 4/2001 | Ratz et al. | |
| 6,528,800 B1 | 3/2003 | Dzwierzynski et al. | |
| 6,555,350 B2 | 4/2003 | Ahring et al. | |
| 6,608,882 B2 | 8/2003 | Allen et al. | |
| 6,620,605 B2 | 9/2003 | Fowler et al. | |
| 6,628,750 B1 | 9/2003 | Korenev | |
| 6,707,049 B1 | 3/2004 | Lyons et al. | |
| 6,713,773 B1 | 3/2004 | Lyons et al. | |
| 6,724,003 B1 | 4/2004 | Doi et al. | |
| 6,780,448 B1 | 8/2004 | Howard | |
| 6,808,600 B2 | 10/2004 | Ross et al. | |
| 6,833,551 B2 | 12/2004 | Avnery | |
| 6,838,678 B1 | 1/2005 | Bujak et al. | |
| 7,019,155 B2 | 3/2006 | Manzer | |
| 7,025,874 B2 | 4/2006 | Chan et al. | |
| 7,153,533 B2 | 12/2006 | Burke et al. | |
| 7,402,428 B2 | 7/2008 | Forster et al. | |
| 7,408,056 B2 | 8/2008 | Medoff et al. | |
| 7,846,295 B1 | 12/2010 | Medoff | |
| 7,867,358 B2 | 1/2011 | Medoff | |
| 7,867,359 B2 | 1/2011 | Medoff | |
| 7,900,857 B2 | 3/2011 | Medoff | |
| 7,931,784 B2 | 4/2011 | Medoff | |
| 7,932,065 B2 | 4/2011 | Medoff | |
| 7,935,219 B2 | 5/2011 | Medoff | |
| 7,971,809 B2 | 7/2011 | Medoff | |
| 8,052,838 B2 | 11/2011 | Medoff | |
| 8,070,912 B2 | 12/2011 | Medoff | |
| 8,074,910 B2 | 12/2011 | Medoff | |
| 8,083,906 B2 | 12/2011 | Medoff | |
| 8,142,620 B2 | 3/2012 | Medoff | |
| 8,147,655 B2 | 4/2012 | Medoff | |
| 8,168,038 B2 | 5/2012 | Medoff | |
| 8,212,087 B2 | 7/2012 | Medoff | |
| 8,221,585 B2 | 7/2012 | Medoff | |
| 8,236,535 B2 | 8/2012 | Medoff et al. | |
| 8,318,453 B2 | 11/2012 | Medoff | |
| 8,415,122 B2 | 4/2013 | Medoff et al. | |
| 8,597,472 B2 | 12/2013 | Medoff | |
| 8,911,833 B2 | 12/2014 | Medoff | |
| 8,951,778 B2 | 2/2015 | Medoff et al. | |
| 2002/0182294 A1 | 12/2002 | Allen et al. | |
| 2003/0094578 A1 | 5/2003 | Nelson | |
| 2003/0094581 A1 | 5/2003 | Rose | |
| 2003/0217383 A1 | 11/2003 | Reuber et al. | |
| 2003/0218414 A1 | 11/2003 | Avnery | |
| 2004/0005674 A1 | 1/2004 | Duck et al. | |
| 2004/0065589 A1 | 4/2004 | Jorgensen | |
| 2004/0113094 A1 | 6/2004 | Lyons et al. | |
| 2004/0173533 A1 | 9/2004 | Farone et al. | |
| 2004/0183032 A1 | 9/2004 | Fink et al. | |
| 2006/0088922 A1 | 4/2006 | Yang et al. | |
| 2006/0196622 A1 | 9/2006 | Trung et al. | |
| 2006/0251764 A1 | 11/2006 | Abbas et al. | |
| 2007/0015855 A1 | 1/2007 | Medoff et al. | |
| 2007/0037259 A1 | 2/2007 | Hennessey et al. | |
| 2007/0040130 A1 | 2/2007 | Nanataki et al. | |
| 2007/0077630 A1 | 4/2007 | Harris et al. | |
| 2007/0134781 A1 | 6/2007 | Agblevor | |
| 2007/0200262 A1 | 8/2007 | Hills | |
| 2007/0215821 A1 | 9/2007 | Stirling et al. | |
| 2008/0227162 A1 | 9/2008 | Varanasi et al. | |
| 2008/0248540 A1 | 10/2008 | Yang | |
| 2008/0313954 A1 | 12/2008 | Lee et al. | |
| 2009/0031026 A1 | 1/2009 | Tanner et al. | |
| 2009/0067575 A1 | 3/2009 | Seppi et al. | |
| 2009/0090654 A1 | 4/2009 | Duyvesteyn et al. | |
| 2009/0120256 A1 | 5/2009 | Pasek | |

(56) References Cited

U.S. PATENT DOCUMENTS

| | | |
|---|---|---|
| 2009/0181433 A1 | 7/2009 | Chotani et al. |
| 2009/0203079 A1 | 8/2009 | Sticklen et al. |
| 2009/0286295 A1 | 11/2009 | Medoff et al. |
| 2009/0321026 A1 | 12/2009 | Medoff |
| 2010/0064746 A1 | 3/2010 | Medoff |
| 2010/0087687 A1 | 4/2010 | Medoff |
| 2010/0093241 A1 | 4/2010 | Medoff |
| 2010/0105119 A1 | 4/2010 | Medoff |
| 2010/0108567 A1 | 5/2010 | Medoff |
| 2010/0112242 A1 | 5/2010 | Medoff |
| 2010/0124583 A1 | 5/2010 | Medoff |
| 2010/0124772 A1 | 5/2010 | Sabesan |
| 2010/0135365 A1 | 6/2010 | Chen et al. |
| 2010/0146870 A1 | 6/2010 | Zeik et al. |
| 2010/0159569 A1 | 6/2010 | Medoff et al. |
| 2010/0179315 A1 | 7/2010 | Medoff |
| 2010/0200806 A1 | 8/2010 | Medoff et al. |
| 2010/0203495 A1 | 8/2010 | Medoff et al. |
| 2010/0206501 A1 | 8/2010 | Medoff |
| 2010/0229256 A1 | 9/2010 | Somleva et al. |
| 2010/0297705 A1 | 11/2010 | Medoff et al. |
| 2010/0297720 A1 | 11/2010 | Medoff et al. |
| 2011/0011960 A1 | 1/2011 | Medoff |
| 2011/0027837 A1 | 2/2011 | Medoff |
| 2011/0039317 A1 | 2/2011 | Medoff |
| 2011/0081335 A1 | 4/2011 | Medoff |
| 2011/0081336 A1 | 4/2011 | Medoff |
| 2011/0107659 A1 | 5/2011 | Gruter et al. |
| 2011/0111456 A1 | 5/2011 | Medoff |
| 2011/0139383 A1 | 6/2011 | Medoff |
| 2011/0155559 A1 | 6/2011 | Medoff |
| 2011/0192989 A1 | 8/2011 | Yaniv et al. |
| 2011/0262985 A1 | 10/2011 | Medoff |
| 2011/0265991 A1 | 11/2011 | Medoff |
| 2011/0287498 A1 | 11/2011 | Medoff et al. |
| 2012/0003704 A1 | 1/2012 | Medoff |
| 2012/0052536 A1 | 3/2012 | Medoff et al. |
| 2012/0074337 A1 | 3/2012 | Medoff |
| 2012/0077247 A1 | 3/2012 | Medoff |
| 2012/0094355 A1 | 4/2012 | Medoff |
| 2012/0094358 A1 | 4/2012 | Medoff |
| 2012/0100577 A1 | 4/2012 | Medoff et al. |
| 2012/0100586 A1 | 4/2012 | Medoff et al. |
| 2012/0142065 A1 | 6/2012 | Medoff |
| 2012/0142068 A1 | 6/2012 | Medoff |
| 2012/0237984 A1 | 9/2012 | Medoff |
| 2012/0309060 A1 | 12/2012 | Medoff |
| 2012/0315675 A1 | 12/2012 | Medoff et al. |
| 2012/0316376 A1 | 12/2012 | Medoff |
| 2012/0322117 A1 | 12/2012 | Anton et al. |
| 2013/0052682 A1 | 2/2013 | Medoff et al. |
| 2013/0052687 A1 | 2/2013 | Medoff et al. |
| 2013/0158302 A1 | 6/2013 | Duff et al. |
| 2014/0011248 A1 | 1/2014 | Medoff et al. |

FOREIGN PATENT DOCUMENTS

| | | |
|---|---|---|
| EP | 2008668 A1 | 12/2008 |
| EP | 2276795 A2 | 1/2011 |
| GB | 721235 A | 1/1955 |
| JP | S49-8692 | 2/1974 |
| JP | 51-138297 | 11/1976 |
| JP | 07-94135 | 4/1995 |
| JP | H08166497 | 6/1996 |
| JP | 11-337700 A | 12/1999 |
| JP | 2001287472 | 10/2001 |
| JP | 2003111356 A | 4/2003 |
| JP | 2005172534 | 6/2005 |
| JP | 2008161137 A | 7/2008 |
| JP | 2010041923 A | 2/2010 |
| JP | 2010506961 | 3/2010 |
| JP | 2011024545 A | 2/2011 |
| RU | 2432400 C2 | 10/2011 |
| WO | WO-95/003374 | 2/1995 |
| WO | 0042620 | 7/2000 |
| WO | WO-2006032282 A1 | 3/2006 |
| WO | WO-2006102543 A2 | 9/2006 |
| WO | WO-2007054610 | 5/2007 |
| WO | WO-2008011598 A2 | 1/2008 |
| WO | WO-2008073186 A2 | 6/2008 |
| WO | 2009001985 | 12/2008 |
| WO | WO-2009134791 A2 | 11/2009 |
| WO | WO-2009155601 A2 | 12/2009 |
| WO | WO-2010135380 A1 | 11/2010 |
| WO | WO-2011063500 | 6/2011 |
| WO | WO-2011081336 | 7/2011 |
| WO | 2011/103033 | 8/2011 |
| WO | WO-2011133536 | 10/2011 |
| WO | WO-2011133536 A1 | 10/2011 |
| WO | WO-2012006438 A2 | 1/2012 |
| WO | WO-2013096693 | 6/2013 |
| WO | WO-2013096700 | 6/2013 |
| WO | WO-2013101977 | 7/2013 |
| WO | WO-2014059113 | 4/2014 |
| WO | WO-2014059140 | 4/2014 |

OTHER PUBLICATIONS

Awafo, V. A., et al., "Effect of Irradiation, as a Pretreatment, on Bioconversion of Corn Stover into Protein-rich Mycelial Biomass of Pleurotus Sajor-Caju," Radiation Physics and Chemistry, vol. 46, No. 4-6, pp. 1299-1302 (Sep. 12, 1995).

Bak, J. S., et al., "Improved enzymatic hydrolysis yield of rice straw using electron beam irradiation pretreatment," Bioresource Technology, vol. 100, No. 3, pp. 1285-1290 (Feb. 2009).

Baucher, M., et al., "Lignin: Genetic Engineering and Impact on Pulping," Critical Reviews in Biochemistry and Molecular Biology, vol. 38, No. 4, pp. 305-350 (Jan. 1, 2003).

Chen, F. and Dixon, R. A., "Lignin Modification Improves Fermentable Sugar Yields for Biofuel Production," Nature Biotechnology, vol. 25, No. 7, pp. 759-761 (Jul. 2007).

Chu, William T., "Overview of Light-Ion Beam Therapy," Columbus-Ohio, ICRU-IAEA Meeting, pp. 1-20 (Mar. 18-20, 2006).

Chunping, Y., et al., "Effect and aftereffect of gamma radiation pretreatment on enzymatic hydrolysis of wheat straw," Bioresource Technology, vol. 99, No. 14, pp. 6240-6245 (Sep. 2008).

De Kerf, M., et al., "Characterization and Disintegration Properties of Irradiated Starch," International Journal of Pharmaceutics, vol. 221, No. 1-2, pp. 69-76 (Jun. 19, 2001).

Eichenberger, C., et al., "7.5 MeV High Average Power Linear Accelerator System for Food Irradiation Applications," Proceedings of the International Symposium on the New Frontier of Irradiated Food and Non-Food Products, KMUTT, Bangkok, Thailand, 8 pages (Sep. 22-23, 2005).

Eriez Magnetics, "How to Choose and Use Vibratory Feeders and Conveyors," 16 pages (2007).

Ghosh, P. and Singh, A., "Physicochemical and Biological Treatments for Enzymatic/Microbial Conversion of Lignocellulosic Biomass," Advances in Applied Microbiology, vol. 39, pp. 295-333 (1993).

Graham-Rowe, Duncan, "Electron Beams Could be Used to Irradiate Post," Daily News, 2 pages (Oct. 24, 2001).

Gromov, A. V., "VI Inter-University Conference on Electron Accelerators," Atomic Energy, vol. 21, No. 2, pp. 143-145 (Aug. 1966).

Han, Y. W., et al., "Chemical and Physical Properties of Sugarcane Bagasse Irradiated with Gamma Rays," J. Agric. Food Chem., vol. 31, No. 1, pp. 34-38 (1983).

Han, Y. W., et al., "Effect of Gamma-Ray Irradiation on Alcohol Production From Corn," Biotechnol. Bioeng., vol. 25, No. 11, pp. 2631-2640 (Nov. 1983).

Hanis T., et al., "Effect of Gamma Irradiation on Survival of Natural Microflora and Some Nutrients in Cereal Meals," Cereal Chemistry, vol. 65, No. 5, pp. 381-383 (1988).

Ibrahim, M. N. M. and Pearce, G. R., "Effects of Gamma Irradiation on the Composition and In Vitro Digestibility of Crop By-products," Agricultural Wastes, vol. 2, pp. 253-259 (Oct.-Dec. 1980).

International Search Report and Written Opinion issued by the European Patent Office as International Searching Authority for International Application No. PCT/US2012/024970 dated Sep. 14, 2012 (19 pages).

(56) References Cited

OTHER PUBLICATIONS

International Search Report and Written Opinion issued by the European Patent Office as International Searching Authority for International Application No. PCT/U52012/025023 dated Apr. 25, 2012 (11 pages).
International Search Report and Written Opinion issued by the U.S. Patent and Trademark Office as International Searching Authority for International Application No. PCT/US2013/064320 dated May 20, 2014 (14 pages).
International Search Report and Written Opinion issued by the U.S. Patent and Trademark Office as International Searching Authority for International Application No. PCT/US2013/064332 dated Feb. 14, 2014 (11 pages).
International Search Report and Written Opinion issued by the U.S. Patent and Trademark Office as International Searching Authority for International Application No. PCT/US2014/021796 dated May 21, 2014 (7 pages).
Iwata, Y., et al., "Alternating-Phase-Focused IH-DTL for Heavy-Ion Medical Accelerators," Proceedings of EPAC 2006, WEPCH169, 08 Applications of Accelerators, Technology Transfer and Industrial Relations, U01 Medical Applications, Edinburgh, Scotland, pp. 2328-2330 (2006).
Kamakura, M. and Kaetsu, I., "Radiation Degradation and the Subsequent Enzymatic Hydrolysis of Waste Papers," Biotechnol. Bioeng., vol. 24, pp. 991-997 (Apr. 1982).
Kang, L., et al., "Bioconversion of kraft paper mill sludges to ethanol by SSF and SSCF," Appl. Biochem. Biotechnol., vol. 161, No. 1-8, pp. 53-66 (May 2010).
Khan, A. W., et al., "Effect of Electron-Beam Irradiation Pretreatment on the Enzymatic Hydrolysis of Softwood," Biotechnol. Bioeng., vol. 28, pp. 1449-1453 (Sep. 1986).
Korolev, A., et al., "Characteristics of Sealed-Off Electron Gun with wide Beam," Proceedings of EPAC 2004, Lucerne, Switzerland, pp. 2727-2729 (2004).
Krane, Kennth S., "Introductory Nuclear Physics," John Wiley & Sons, Inc., 858 pages (1988).
Kumar, P., et al., "Methods for Pretreatment of Lignocellulosic Biomass for Efficient Hydrolysis and Biofuel Production," Ind. Eng. Chem. Res., vol. 48, No. 8, pp. 3713-3729 (Jan. 1, 2009).
Leitner, M. A., et al., "Status of the Superconducting ECR Ion Source Venus," Proceedings of the EPAC 2000, Vienna, Austria, 3 pages (2000).
Leonhardt, J. W., et al., "Gamma and Electron Radiation Effects on Straw," Radial. Phys. Chem., vol. 21, No. 4, pp. 397-400 (1983).
Levy, I., et al., "Modification of polysaccharides and plant cell wall by endo-1,4-beta-glucanase and cellulose-binding domains," Biomolecular Engineering, vol. 19, No. 1, pp. 17-30 (Jun. 2002).
McMillan, Gregory J., "Analysis of Vibratory Equipment Using the Finite Element Method," A Research Paper Submitted in Partial Fulfillment of the Requirements for the Master of Science Degree in Manufacturing Engineering; The Graduate School University of Wisconsin-Stout, 59 pages (May 2011).
Miyamoto, Kazuhisa, "Chapter 3.2 Cellulase Production," Renewable Biological Systems for Alternative Sustainable Energy Production, FAO Agricultural Services Bulletin, #128, 13 pages (1997).
Philippidis, G. P., "Cellulose bioconversion technology," Chapter 12 in Handbook on Bioethanol: Production and Utilization, Taylor & Francis, Washington, D.C., 35 pages (1996).
Prelec, Krsto, "Ions and Ion Accelerators for Cancer Treatment," FIZIKA B, vol. 6, No. 4, pp. 177-206 (1997).
Saleh, F., et al., "Carbohydrases are Digested by Proteases Present in Enzyme Preparations During in vitro Digestion," J. Poultry Sci., vol. 41, pp. 229-235 (2004).
Sarath, G., et al., "Opportunities and roadblocks in utilizing forages and small grains for liquid fuels," J. Ind. Microbial. Biotechnol., vol. 35, pp. 343-354 (2008).
Scharf, W. and Wieszczycka, W., "Electron Accelerators for Industrial Processing—a Review", 15th International Conference on the Applications of Accelerators in Research and Industry, Denton, TX, USA, pp. 949-952 (1999).

Seiboth, B., et al., "Chapter 13: Trichoderma reesei: A Fungal Enzyme Producer for Cellulosic Biofuels," Biofuel Production—Recent Developments and Prospects, pp. 309-340, 33 pages (2011).
Smith, G. S., et al., "Irradiation Enhancement of Biomass Conversion," Radiation Physics and Chemistry, vol. 25, Nos. 1-3, pp. 27-33 (Jan. 1, 1985).
Stevens, Robert W., "On the Stowage of Ships and Their Cargoes," Section 190 Fermentation, Nabu Press, 3 pages (Jan. 7, 2010).
Taherzadeh, M. J. and Karimi, K., "Pretreatment of Lignocellulosic Wastes to Improve Ethanol and Biogas Production: A Review," Int. J. Mol. Sci., vol. 9, pp. 1621-1651 (2008).
Tewari, H. K., et al., "Role of Pretreatments on Enzymatic Hydrolysis of Agricultural Residues for Reducing Sugar Production," J. Chem. Tech. Biotechnol., vol. 38, No. 3, pp. 153-165 (1987).
Wang, J. S., et al., "Efficient Cellulase Production from Corn Straw by Trichoderma Reesei LW1 Through Solid State Fermentation Process," Ethnobotanical Leaflets, vol. 2005, No. 1, Article 7 (2005).
Wayman, M., et al., "Bioconversion of Waste Paper to Ethanol," Process Biochemistry, vol. 27, No. 4, pp. 239-245 (Jul. 1992).
Whitham, K., et al., "12 MW, 100 KW, 7000 Hour/Year Modulator for Titan Scan," Tenth IEEE International Pulsed Power Conference, Digest of Technical Papers, vol. 1, pp. 534-538 (Jul. 3-6, 1995).
Wilson, Ian, "Filler and Coating Pigments for Papermakers," Industrial Minerals and Rocks: Commodities, Markets and Uses, Part III, No. 96, pp. 1287-1300 (2006).
Xia, L., et al., "Saccharification of Corn Stover by Immobilized Trichoderma reesei cells," Wei Shen Wu Xue Bao, vol. 38, No. 2, pp. 114-119 (Apr. 1998).
Yamada, N., et al., "Decomposition Behavior of Waste Paper with Hot Compressed Water," Journal of the Japan Institute of Energy, vol. 79, No. 6, pp. 540-547 (Jun. 2000).
Carter et al., "Removal and Recovery of Furfural, 5-Hydroxymethylfurfural, and Acetic Acid From Aqueous Solutions Using a Soluble Polyelectrolyte," Biotechnology and Bioengineering, vol. 108, No. 9, pp. 2046-2052 (2011).
Dias et al., "Modified versions of sulfated zirconia as catalysts for the conversion of xylose to furfural," Catalysis Letters, vol. 114, No. 3-4, pp. 151-160 (Apr. 2007).
English translation of Search Report issued by the Eurasian Patent Office in EA Patent No. 201591308, completed Feb. 19, 2016 (1 page).
Extended European Search Report issued by the European Patent Office for Application No. 13845680.1 dated Jun. 28, 2016 (7 pages).
Extended European Search Report issued in EP14759993.0, dated Apr. 28, 2016 (6 pages).
International Search Report and Written Opinion issued by the European Patent Office as International Search Authority for International Application No. PCT/US2010/023957 dated Jan. 3, 2011 (17 pages).
International Search Report and Written Opinion issued by the U.S. Patent and Trademark Office as International Searching Authority for International Application No. PCT/US2013/049265 dated Dec. 23, 2013 (9 pages).
International Search Report and Written Opinion issued by the U.S. Patent and Trademark Office as International Searching Authority for International Application No. PCT/US2013/064317 dated Mar. 7, 2014 (9 pages).
International Search Report and Written Opinion issued by the U.S. Patent and Trademark Office as International Searching Authority in International Application No. PCT/US2014/021629, dated Jul. 11, 2014 (6 pages).
International Search Report and Written Opinion issued by the U.S. Patent and Trademark Office as International Searching Authority in PCT/US2014/021609, dated May 22, 2014 (9 pages).
Kang et al., "Production of cellulases and hemicellulases by *Aspergillus niger* KK2 from lignocellulosic biomass," Bioresource Technology, vol. 91, pp. 153-156 (2004).
Khan et al., "Electron beam irradiation pretreatment and enzymatic saccharification of used newsprint and paper mill wastes," Interna-

(56) References Cited

OTHER PUBLICATIONS tional Journal of Radiation Applications and Instrumentation. Part C. Radiation Physics and Chemistry, vol. 29, Issue 2, pp. 117-120 (1987).

Moreau et al., "Selective preparation of furfural from xylose over microporous solid acid catalysts," Industrial Crops and Products, vol. 7, pp. 95-99 (1998).

Mosier et al., "Features of promising technologies for pretreatment of lignocellulosic biomass," Bioresource Technology, vol. 96, pp. 673-686 (2005).

Palmqvist and Hahn-Hägerdal, "Fermentation of lignocellulosic hydrolysates. II: inhibitors and mechanisms of inhibition," Bioresource Technology, vol. 74, pp. 25-33 (2000).

Search Report issued by the Intellectual Property Office of Singapore in SG Patent No. 11201502353T, completed Apr. 20, 2016 (2 pages).

Search Report issued in related Singaporean Patent Application No. 11201502092X, date of completion Dec. 11, 2015 (3 pages).

Sluiter et al., "Compositional Analysis of Lignocellulosic Feedstocks. 1. Review and Description of Methods," Journal of Agricultural and Food Chemistry, vol. 58, pp. 9043-9053 (2010).

Tao et al., "Efficient process for the conversion of xylose to furfural with acidic ionic liquid," Can. J. Chem, vol. 89, pp. 83-87 (Dec. 13, 2010).

Wooley et al., "A Nine-Zone Simulating Moving Bed for the Recovery of Glucose and Xylose from Biomass Hydrolyzate," Ind. Eng. Chem. Res., vol. 37, pp. 3699-3709 (1998).

Written Opinion issued in related Singaporean Patent Application No. 11201502092X, dated Feb. 19, 2016 (6 pages).

Office Action dated Aug. 8, 2017, issued by the Japanese Patent Office in related JP Application No. 2015-536893 (3 pages).

Industrial Electron Accelerator and its Application in Radiation Processing, Translated by Zhao Weijiang et al., Atomic Energy Press, 1st Edition in Dec. 1996.

Solid Waste Treatment and Recycling, editor-in-chief: Li Guoxue, China Environmental Science Press, 1st Edition in Jul. 2005.

Notification of Reexamination—Corresponding Chinese Application No. 201380051055.9, dated Jun. 28, 2018, 8 pages.

Notification of Reexamination from corresponding CN Application No. 201380051055.9, dated Jun. 28, 2018, 16 pages.

"Evidence 1" cited in Notification of Reexamination from corresponding CN Application No. 201380051055.9, "Industrial Electron Accelerator and its Application in Radiation Processing," Atomic Energy Press, 1st Edition, Dec. 1996, 84 pages.

"Evidence 2" cited in Notification of Reexamination from corresponding CN Application No. 201380051055.9, "Solid Waste Treatment and Recycling," China Environmental Science Press, 1st Edition, Jul. 2005, 95 pages.

Examination Report issued on New Zealand Application No. 740766, dated Jul. 18, 2019, 3 pages.

Examination Report issued on New Zealand Application No. 747168, dated Jul. 18, 2019, 3 pages.

\* cited by examiner

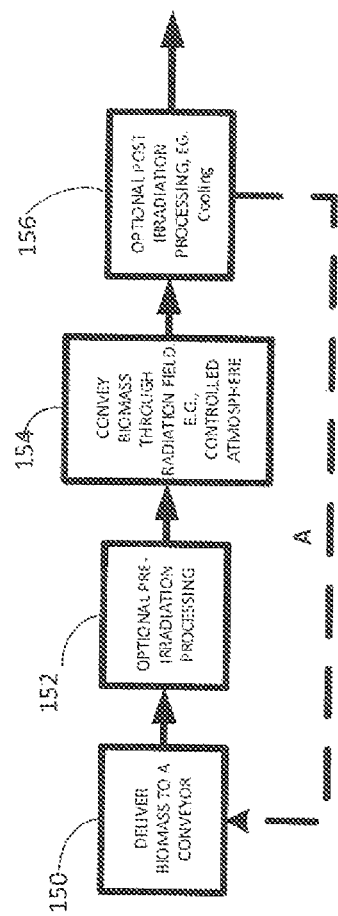

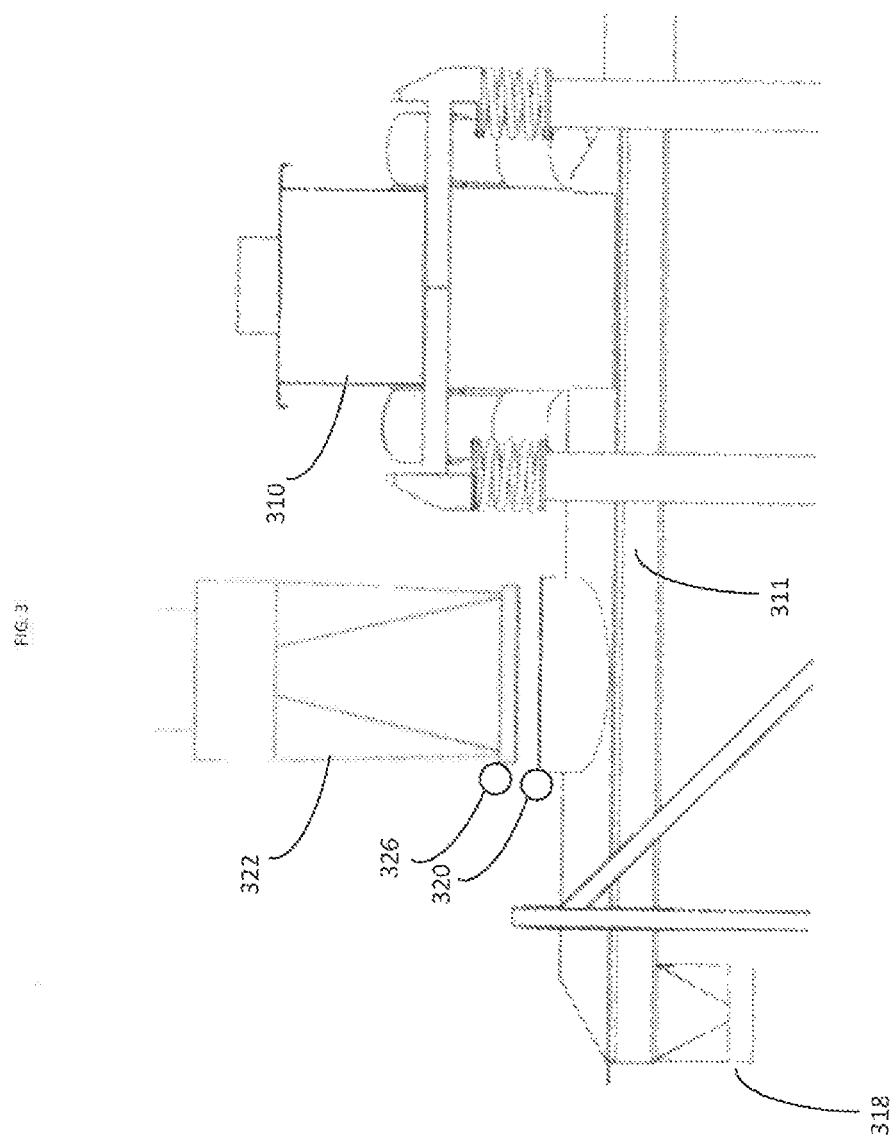

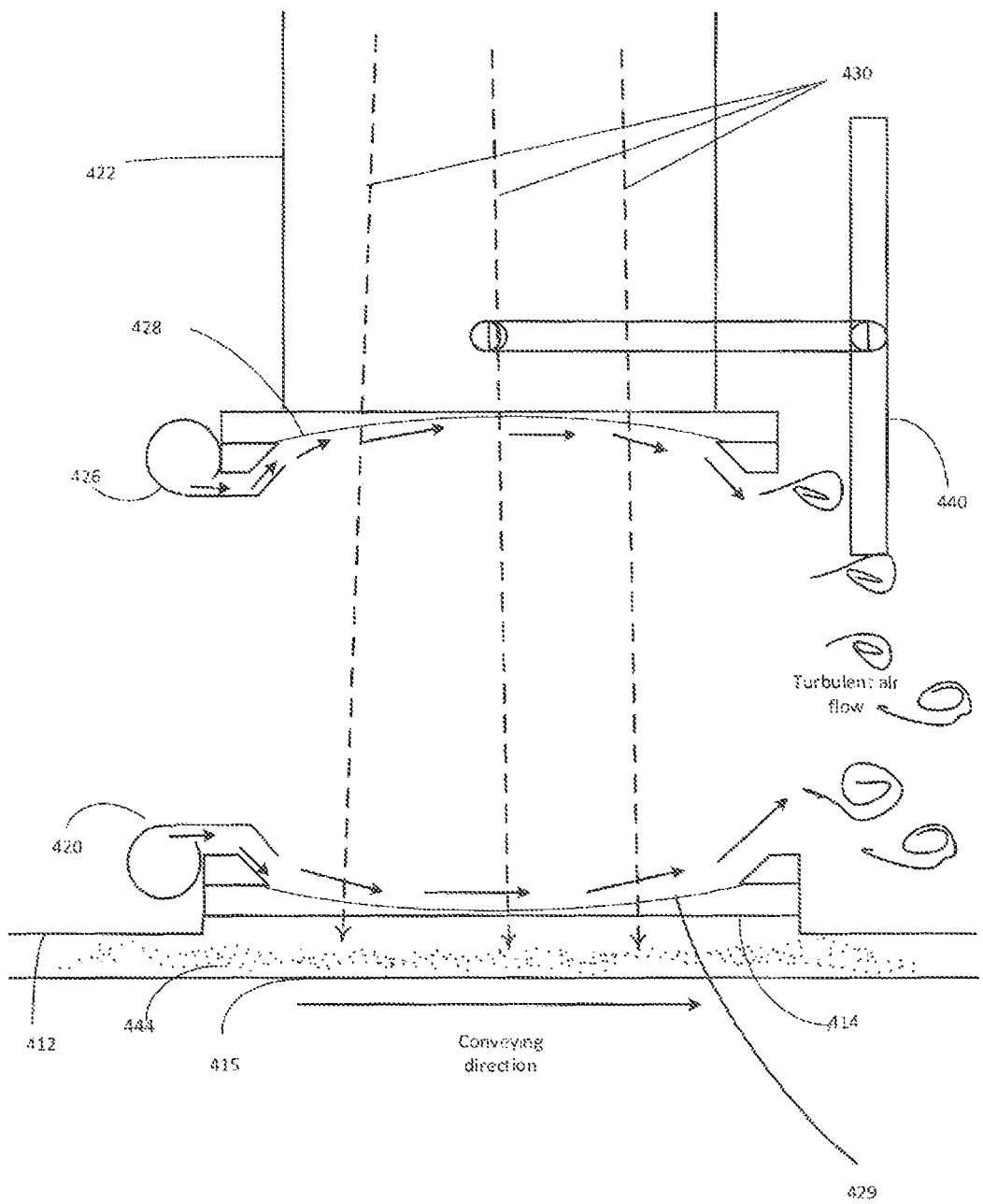

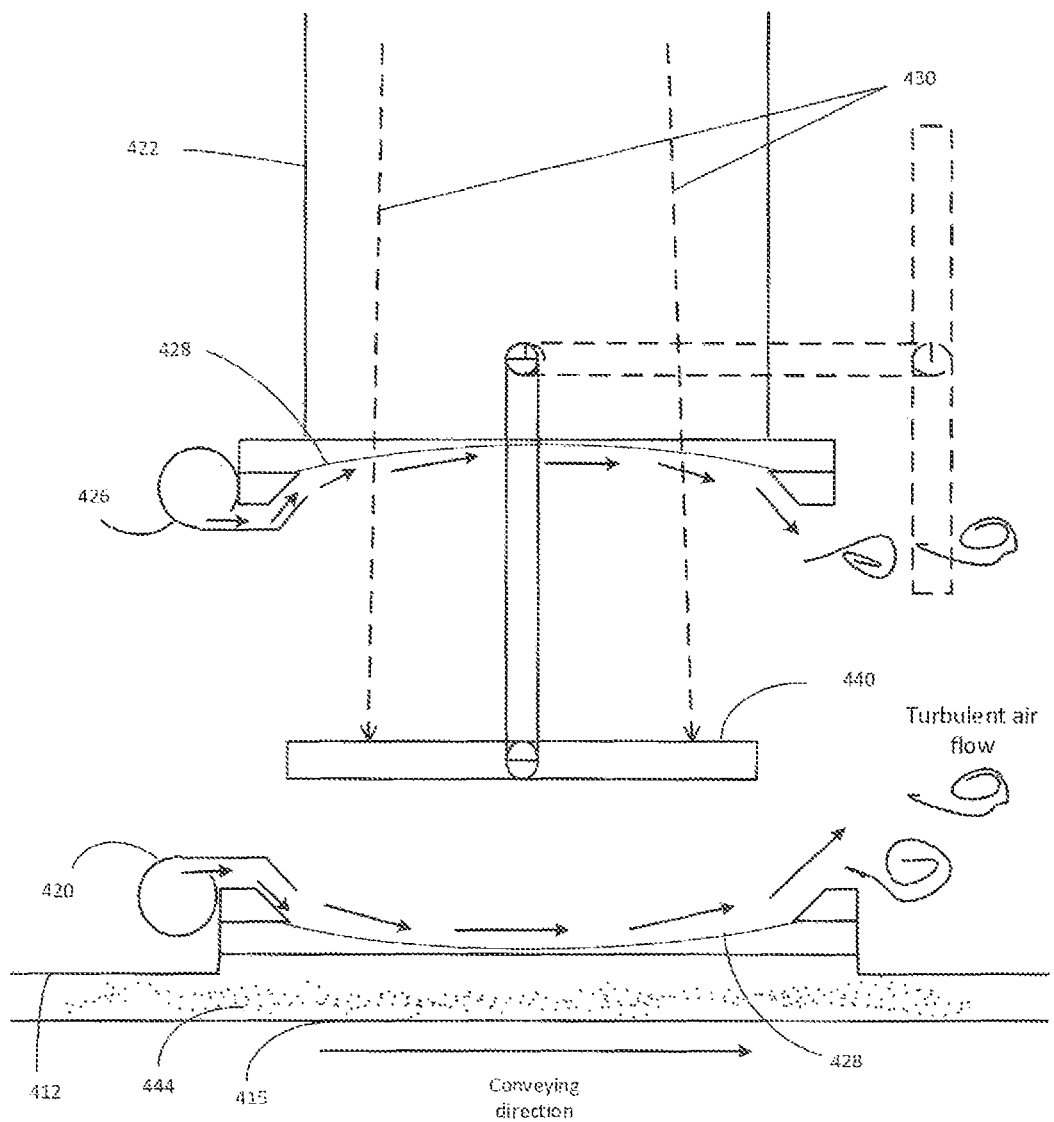

TREATING BIOMASS

This application is a continuation application of U.S. patent application Ser. No. 14/434,682, filed on Apr. 9, 2015, which is a National Stage of International Patent Application No. PCT/US2013/064332 filed on Oct. 10, 2013, which claims priority to U.S. Provisional Application Ser. No. 61/711,807 filed on Oct. 10, 2012, and U.S. Provisional Application Ser. No. 61/711,801 filed on Oct. 10, 2012. The entire disclosures of these applications are incorporated by reference herein.

BACKGROUND

As demand for petroleum increases, so too does interest in renewable feedstocks for manufacturing biofuels and biochemicals. The use of lignocellulosic biomass as a feedstock for such manufacturing processes has been studied since the 1970s. Lignocellulosic biomass is attractive because it is abundant, renewable, domestically produced, and does not compete with food industry uses.

Many potential lignocellulosic feedstocks are available today, including agricultural residues, woody biomass, municipal waste, oilseeds/cakes and sea weeds, to name a few. At present these materials are either used as animal feed, biocompost materials are burned in a cogeneration facility or are landfilled.

Lignocellulosic biomass comprises crystalline cellulose fibrils embedded in a hemicellulose matrix, surrounded by lignin. This produces a compact matrix that is difficult to access by enzymes and other chemical, biochemical and biological processes. Cellulosic biomass materials (i.e., biomass material from which the lignin has been removed) is more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

While a number of methods have been tried to extract structural carbohydrates from lignocellulosic biomass, they are either are too expensive, produce too low a yield, leave undesirable chemicals in the resulting product, or simply degrade the sugars.

Monosaccharides from renewable biomass sources could become the basis of chemical and fuels industries by replacing, supplementing or substituting petroleum and other fossil feedstocks. However, techniques need to be developed that will make these monosaccharides available in large quantities and at acceptable purities and prices.

SUMMARY

Described herein are methods for treating a biomass material, where the method includes passing an electron beam through multiple window foils and into the biomass material. The multiple window foils can include a system of cooled window foils.

In another implementation the invention pertains to methods and systems for cooling a primary and secondary foil window of a scanning type electron beam accelerator.

In one embodiment, the invention pertains to methods and systems for cooling a primary and secondary foil window of a scanning type electron beam accelerator and irradiating a material (e.g., a biomass material).

A method is provided for producing a treated biomass material, where the method includes: providing a starting biomass material; and passing an electron beam through multiple window foils into starting biomass material; thereby producing a treated biomass material. The treated biomass material can have a lower level of recalcitrance relative to the starting biomass material. The multiple window foils can include a system of gas cooled window foils.

Also provided is a system for cooling multiple single-type window foils of an electron beam accelerator, where the system includes: a first flow path for providing a first cooling gas across a primary single-type window foil and second flow path for providing a second cooling gas across a secondary single-type window foil, where the primary and secondary single-type window foils are positioned with a gap of less than about 9 cm between them. Alternately, if the energy of electron beam accelerator is high, than larger gaps can be used. Gaps as large as 75 cm can be used.

Also provided is a method for cooling multiple single-type window foils of an electron beam accelerator, where the methods includes: passing a first cooling gas across a primary single-type window foil and passing a second cooling gas across a secondary single-type window foil, where the primary and secondary single-type window foils are positioned facing each other with a gap of less than about 9 cm between them.

The system of gas cooled window foils can include: a primary single-type window foil attached to a scanning horn of an electron beam accelerator; a secondary single-type window foil positioned on an atmospheric side of the scanning horn; a first flow path providing a first cooling gas across the primary single-type window foil; a second flow path providing a second cooling gas across the secondary single-type window foil; and a gap between the primary single-type window foil and the secondary single-type window foil. The system of gas cooled window foils can further include: a cooling chamber having an interior volume defined by one or more walls, the primary single-type window foil and the secondary single-type window foil, wherein the cooling chamber include: a first inlet, which allows a first cooling gas to enter the interior volume; an optional second inlet, which allows optionally a second cooling gas to enter the interior volume; and at least one outlet, which allows the first and the second cooling gasses to exit the interior volume. The cooling chamber can include four walls and the interior volume can be approximately rectangular prism in shape. The system of gas cooled window foils can further include a treatment enclosure with a cover surface, where the enclosure is positioned on a side of the secondary single-type window foil opposite the electron beam accelerator. The secondary single-type window foil can be mounted on the cover surface. The cover surface can be perpendicular to the electron beam accelerator. The treatment enclosure can have a first opening.

The methods and systems can also include the steps of: conveying the biomass material through the first opening; positioning the biomass material under the secondary single-type window foil; and irradiating the biomass material; thereby producing a treated biomass material. The treatment enclosure can include a second opening. The method can include the step of conveying the treated biomass material out of the treatment enclosure through the second opening. Positioning the biomass can be instantaneous, that is, the positioning step can include conveying the material on a conveyer belt that is continuously moving.

The method can also include purging the treatment enclosure with an inert gas, or a reactive gas.

The primary single-type window foil can be made from an element selected from the group consisting of: titanium, scandium, vanadium, chromium, nickel, zirconium, niobium, molybdenum, ruthenium, rhodium, palladium, hafnium, tantalum, tungsten, rhenium, platinum, iridium, and alloys or mixtures of any of these.

Alternatively, the secondary single-type window foil can be made from an element selected from the group consisting of: titanium, scandium, vanadium, chromium, nickel, zirconium, niobium, molybdenum, ruthenium, rhodium, palladium, hafnium, tantalum, tungsten, rhenium, platinum, iridium, beryllium, aluminum, silicon, and alloys or mixtures of any of these.

The primary single-type window foil and the secondary single-type window foil can be made of the same element, alloy, or mixture, or they can be made of different elements, alloys, or mixtures. The primary single-type window foil or the secondary single-type window foil or both can be made from a low Z element. The primary single-type window foil can be made from a high Z element and the secondary single-type window foil can be made from a low Z element.

The primary single-type window foil can be from 10 to 50 microns thick, from 15 to 40 microns thick, from 20 to 30 microns thick, from 5 to 30 microns thick, from 8 to 25 microns thick, or from 10 to 20 microns thick. The single-type window foils can be the same thickness, or different thickness.

The starting biomass material is selected from the group consisting of: cellulosic material, lignocellulosic material, and starchy material. The biomass can be paper, paper products, paper waste, wood, particle board, sawdust, agricultural waste, sewage, silage, grasses, wheat straw, rice hulls, bagasse, cotton, jute, hemp, flax, bamboo, sisal, abaca, straw, corn cobs, corn stover, alfalfa, hay, coconut hair, seaweed, algae, and mixtures thereof.

The biomass can be treated with between 10 and 200 Mrad of radiation, between 10 and 75 Mrad of radiation, between 15 and 50 Mrad of radiation, or between 20 and 35 Mrad of radiation.

The electron beam can include electrons having an energy of about 0.5-10 MeV, about 0.8-5 MeV, about 0.8-3 MeV, about 1-3 MeV, or about 1 MeV.

The electron beam can have a beam current of at least about 50 mA, at least about 60 mA, at least about 70 mA, at least about 80 mA, at least about 90 mA, at least about 100 mA, at least about 125 mA, at least about 150 mA.

The electron beam can include electrons having an energy of about 1 MeV, and the spacing between the primary single-type window foil and the secondary single-type window foil can be less than about 30 centimeters. The electron beam can include electrons having an energy of about 1 MeV, and the spacing between the primary single-type window foil and the secondary single-type window foil can be less than 20 centimeters. The electron beam can include electrons having an energy of about 1 MeV, and the spacing between the primary single-type window foil and the secondary single-type window foil can be less than 10 centimeters.

Alternatively, the electron beam comprises electrons can have an energy of about 5 MeV, and the spacing between the primary single-type window foil and the secondary single-type window foil can be less than 75 centimeters. The electron beam comprises electrons can have an energy of about 5 MeV, and the spacing between the primary single-type window foil and the secondary single-type window foil can be less than 60 centimeters. The electron beam comprises electrons can have an energy of about 5 MeV, and the spacing between the primary single-type window foil and the secondary single-type window foil can be less than 50 centimeters. The electron beam comprises electrons can have an energy of about 5 MeV, and the spacing between the primary single-type window foil and the secondary single-type window foil can be less than 40 centimeters. The electron beam comprises electrons can have an energy of about 5 MeV, and the spacing between the primary single-type window foil and the secondary single-type window foil can be less than 30 centimeters. The electron beam comprises electrons can have an energy of about 5 MeV, and the spacing between the primary single-type window foil and the secondary single-type window foil can be less than 20 centimeters.

The methods and systems described herein can include a beam stop.

One advantage of the methods and systems discussed herein is that the processes are more robust and incur less down time from failure of foil windows. In particular, multiple window systems greatly reduce the likelihood of primary window failure/implosion, which can destroy expensive accelerator parts. Another advantage is that there can be a reduction in the production of toxic by-products, relative to some conventional processes. These advantages provide safer and more robust processing, e.g., higher and safer throughput in producing useful products. Yet another advantage of some of the methods and systems described is that cooling of foil windows can done with a high flow rate of cooling gas without disturbing the material targeted for irradiation. Another advantage of some of the methods and systems is that the gap between window foils allows for a beam stop to be removable placed between the windows.

Implementations of the invention can optionally include one or more of the following summarized features. In some implementations, the selected features can be applied or utilized in any order while in others implementations a specific selected sequence is applied or utilized. Individual features can be applied or utilized more than once in any sequence. In addition, an entire sequence, or a portion of a sequence, of applied or utilized features can be applied or utilized once or repeatedly in any order. In some optional implementations, the features can be applied or utilized with different, or where applicable the same, set or varied, quantitative or qualitative parameters as determined by a person skilled in the art. For example, parameters of the features such as size, individual dimensions (e.g., length, width, height), location of, degree (e.g., to what extent such as the degree of recalcitrance) duration, frequency of use, density, concentration, intensity and speed can be varied or set, where applicable as determined by a person of skill in the art.

A method irradiating a biomass material by passing an electron beam through multiple windows into the biomass material. The recalcitrance of the biomass is reduced by the irradiating. At least one of the multiple windows is a metallic foil. The primary single-type window foil is on the high vacuum side of the scanning horn of the electron beam accelerator and a secondary window is positioned on the atmospheric side of the scanning horn. In one aspect, the primary single type window foil and the secondary window are part of the same electron beam structure and the foils are cooled by cooling gas. In one configuration both the primary and secondary window foil has cooling gas. In another aspect the primary window foil is on the vacuum side of the scanning horn of the electron beam accelerator and there is a treatment enclosure with a cover surface, where the enclosure is positioned on a side of the secondary single-type window foil opposite the electron beam accelerator, and the secondary single-type window foil is mounted on the cover surface, perpendicular to the electron beam accelerator and mechanically integral to the treatment enclosure.

A method of processing biomass where the biomass is conveyed into a first opening of the treatment enclosure, positioned under the secondary single type window foil and irradiating it, followed by conveying the irradiated biomass out the second opening of the enclosure. The gaseous space of treatment enclosure can be purged with an inert gas, a reactive gas or mixtures of these.

The window foils may be made from an element selected from the group consisting of: titanium, scandium, vanadium, chromium, nickel, zirconium, niobium, molybdenum, ruthenium, rhodium, palladium, hafnium, tantalum, tungsten, rhenium, platinum, iridium, beryllium, aluminum, silicon, and alloys or mixtures of any of these. The window foils may be made up the same or different elements, or alloys as listed previously. The window foils can be made of a low Z element and the single-type primary window can be made of a high Z element. The primary single-type window foil is from 10 to 50 microns thick, alternately 15 microns to 40 microns, optionally 20 to 30 microns thick. The secondary single-type window foil is from 5 to 30 microns thick, alternately 8 microns to 25 microns, optionally 10 to 20 microns thick. The window foils may be of different thickness.

The starting biomass material is selected from the group consisting of: cellulosic material, lignocellulosic material, and starchy material and can be selected from the group consisting of paper, paper products, paper waste, wood, particle board, sawdust, agricultural waste, sewage, silage, grasses, wheat straw, rice hulls, bagasse, cotton, jute, hemp, flax, bamboo, sisal, abaca, straw, corn cobs, corn stover, alfalfa, hay, coconut hair, seaweed, algae, and mixtures thereof. The biomass is treated with between 10 and 200 Mrad of radiation, optionally 10 to 75 Mrad, alternatively 15 to 50 Mrad and further optionally 20 to 35 Mrad. The biomass is treated where the electron beam has an energy of between 0.5 to 10 MeV, optionally 0.8 to 5 MeV, alternatively 0.8 to 3 MeV and further optionally 1 to 3 MeV. The biomass is treated where the electron beam has a beam current of at least 50 mA, alternatively, at least 60 mA, optionally, at least 70, further optionally at least 80 mA, alternately, at least 90 mA, alternately, at least 100 mA, optionally at least 125 mA and further optionally at least 150 mA. The biomass is treated with an electron beam with electrons about 1 MeV and the spacing between the primary single-type window foil and secondary single-type window foil is less than 30 centimeters, alternately, where the spacing is less than 20 centimeters, and optionally where the spacing is less than 10 centimeters. Alternately, when the an electron beam with electrons about 5 MeV and the spacing between the primary single-type window foil and secondary single-type window foil is less than 75 centimeters, alternately, where the spacing is less than 60 centimeters, and optionally, where the spacing is less than 50 centimeters and optionally where the spacing is less than 40 centimeters, and alternately 30 and alternately less than 20 centimeters.

The method of treating where the electron beam accelerator has a beam stop which can be moveable to absorb different levels of electrons. The beam stop and its configuration can absorb 10%, 20%, 40%, 60% 80% and 96% of the incident electron energy.

Other features and advantages of the methods and systems will be apparent from the following detailed description, and from the claims.

DESCRIPTION OF DRAWINGS

FIG. 2 is a diagram showing exemplary processing including irradiation of biomass in an inert atmosphere.

FIG. 3 is an illustration of an enclosed conveyor for irradiating a biomass feedstock.

FIG. 4B shows a different configuration of the blow up cross section including a beam stop. FIG. 4C is a blow up cross section illustration of the enclosed conveyor with the pivoting beam stop blocking the electrons.

DETAILED DESCRIPTION

Described herein is a method for irradiating biomass material, which facilitates the conversion of the material into useful products and improves the yield of those products from the biomass material. The treatment methods described herein are therefore useful in producing a biomass feedstock for use in other processes.

The methods disclosed herein can effectively lower the recalcitrance level of the biomass material, improving its utility as a feedstock in the production of useful intermediates and products. The claimed methods make the biomass material easier to process by methods such as bioprocessing (e.g., with any microorganism described herein, such as a homoacetogen or a heteroacetogen, and/or any enzyme described herein), thermal processing (e.g., gasification or pyrolysis) or chemical processing (e.g., acid hydrolysis or oxidation). Biomass material intended for use as a feedstock can be treated or processed using one or more of any of the methods described herein, such as mechanical treatment, chemical treatment, radiation, sonication, oxidation, pyrolysis or steam explosion. The various treatment systems and methods can be used in combinations of two, three, or even four or more of these technologies or others described herein and elsewhere.

Figure 1:
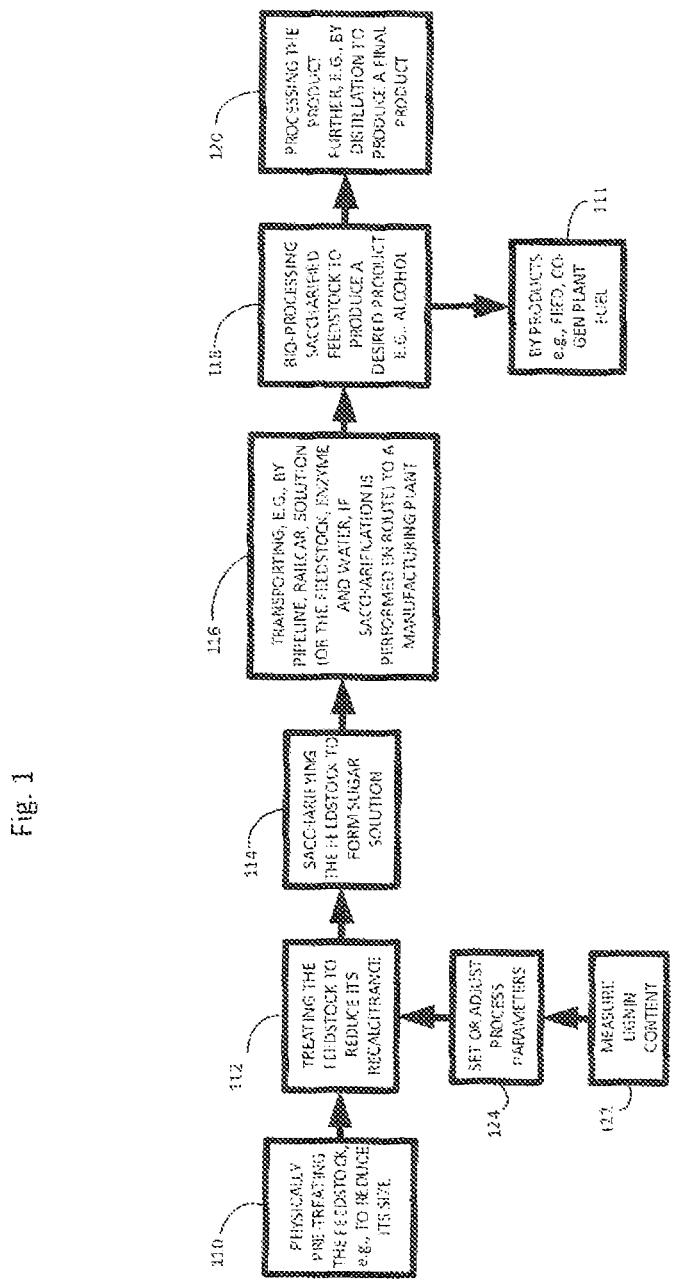
FIG. 1 is a diagram showing exemplary processing of biomass materials to useful products.

Saccharified biomass can then be manufactured into various products. For example, FIG. 1, shows a process for manufacturing a sugar and other useful products (e.g., alcohol). The process can include, for example, optionally mechanically treating a feedstock (step 110), before and/or after this treatment, treating the feedstock with another physical treatment, for example irradiation by the methods described herein, to further reduce its recalcitrance (step 112), and saccharifying the feedstock, to form a sugar solution (step 114). Optionally, the method may also include transporting, e.g., by pipeline, railcar, truck or barge, the solution (or the feedstock, enzyme and water, if saccharification is performed en route) to a manufacturing plant (step 116). In some cases the saccharified feedstock is further bioprocessed (e.g., fermented) to produce a desired product (step 118) and byproduct (111). The resulting product may in some implementations be processed further, e.g., by distillation (step 120). If desired, the steps of measuring lignin content (step 122) and setting or adjusting process parameters based on this measurement (step 124) can be performed at various stages of the process, as described in U.S. Pat. App. Pub. 2010/0203495 A1, filed on Feb. 11, 2010, the entire disclosure of which is incorporated herein by reference.

FIG. 2 shows an irradiation process. This process can be part of the process described in FIG. 1 or it can be part of a separate process. Initially, biomass can be delivered to a conveyor (150). Optionally, the conveyor can be enclosed. The biomass can be pre-irradiation processed while enclosed in the enclosed conveyor or prior to enclosing the material in the enclosed conveyor. Advantageously, the biomass on the conveyor when in an treatment enclosure, is protected from rapid air currents that can cause the biomass (e.g., fines and dust) to be lofted in the air. This can present an explosion hazard or damage equipment. The biomass can be conveyed through an irradiation zone (e.g., radiation field) (154). After irradiation, the biomass can be post processed (156). The process can be repeated (e.g., dashed arrow A). Finally the irradiated biomass is removed from the conveyor and either collected for later processing or sent directly to make useful products.

FIG. 3 shows one embodiment, an enclosed conveying system for irradiating a comminuted biomass. The enclosure has an enclosed distribution system (310), an enclosed conveyor (311), material removal system (318) where the irradiated material exits the conveyor and an irradiation vault and a scan horn (322). The electron window foil (not shown) and enclosure window foil (not shown) have window coolers (320) and (326) respectively for blowing air across the surface of the windows. The enclosed material distribution system (310) distributes the biomass onto the conveyor and brings the biomass from outside of the irradiation vault into the enclosed stainless steel conveyor without generating dust outside of the enclosure (e.g., protecting the biomass from air from the window cooling system). The distribution system can be equipped with a spreading system (not shown) to evenly distribute the biomass on the conveyor to a depth of about 0.25 inches. The enclosed removal system (318) allows the material to fall off of the conveyor belt without generating dust outside of the enclosure, where the material can be collected (e.g., outside the irradiation vault) or directed elsewhere for further processing. The scan horn window and enclosure window can be brought together, or lined up so that the electron beams pass thought the scan horn window, through a small gap of cooling air and then through the enclosure window. For example, the conveyor can be aligned by moving it on casters and then fixing it in place. For example the casters can be blocked with a permanent break, a block, and or a depression. The conveyor can also be aligned by other methods and equipment, for example rails, wheels, pulleys, shims e g, in any combination. In this window arrangement the scan horn window and enclosure window do not touch, so that the remaining gap allows for efficient cooling. The scan horn window is part of the electron beam apparatus and the enclosure window is part of the treatment enclosure system.

Figure 4A:
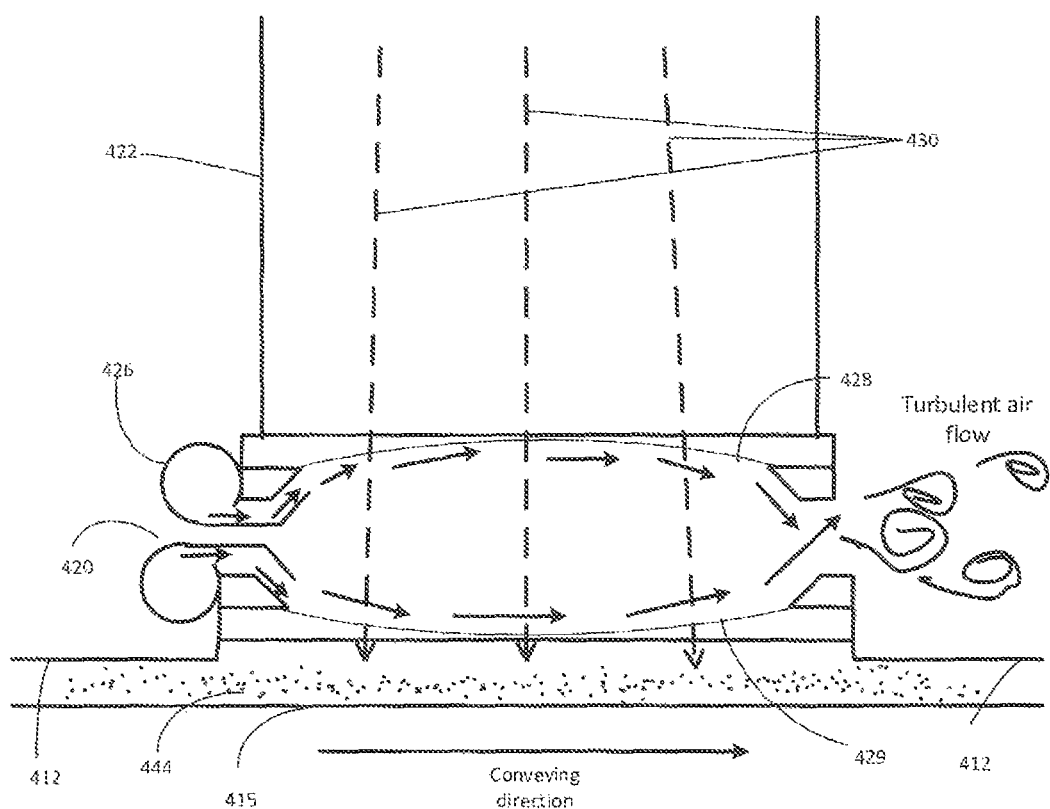
FIG. 4A is a blow up cross section illustration of the enclosed conveyor and scanning horn with cooled windows.

A cross sectional detailed view of the scan horn and scan horn window of FIG. 3 are shown in FIG. 4A. The scan horn window cooler (426) and enclosure window cooler (420) blow air at high velocity across the windows as indicted by the small arrows. The electrons in the electron beam (430) pass through the vacuum of the scan horn (422) through the scan horn window (428), through the cooling air gap between the scan horn window and enclosure window, through the enclosure window (429) and impinge on and penetrate the biomass material (444) on the conveyor surface (415). The scan horn window is shown as curved towards the vacuum side of the scan horn, for example due to the vacuum. In the embodiment illustrated, the enclosure window is curved towards the conveyed material. The curvature of the windows can help the cooling air path flow past the window for efficient cooling. The enclosure window is mounted on the cover (412) of the enclosed conveyor. The enclosure window is aligned with the cover surface.

FIG. 4B shows a different configuration of the detailed cross section view of the enclosed conveyor including a beam stop. A beam stop (440) can be pivotally fixed to the scan horn and is shown in the open position, e.g., allowing the e-beam to impinge on the conveyed material. FIG. 4C shows the cross sectional blowup of the scan horn and scan horn window with a beam stop (440) where the beam stop is in position for blocking the electrons. The cover surface is denoted by 414.

Optionally, the conveying system shown in FIG. 3 can be maintained under an atmosphere of an inert or reactive gas by a gentle purge through an inlet connected to a nitrogen gas source. The inlet can be positioned at different locations, for example, close to the zone where the biomass is irradiated to be more effective in reducing ozone formation if purging is with an inert gas; or further and downstream of the irradiation if a reactive gas is used that is designed to reacted with an irradiated material.

Figure 5:
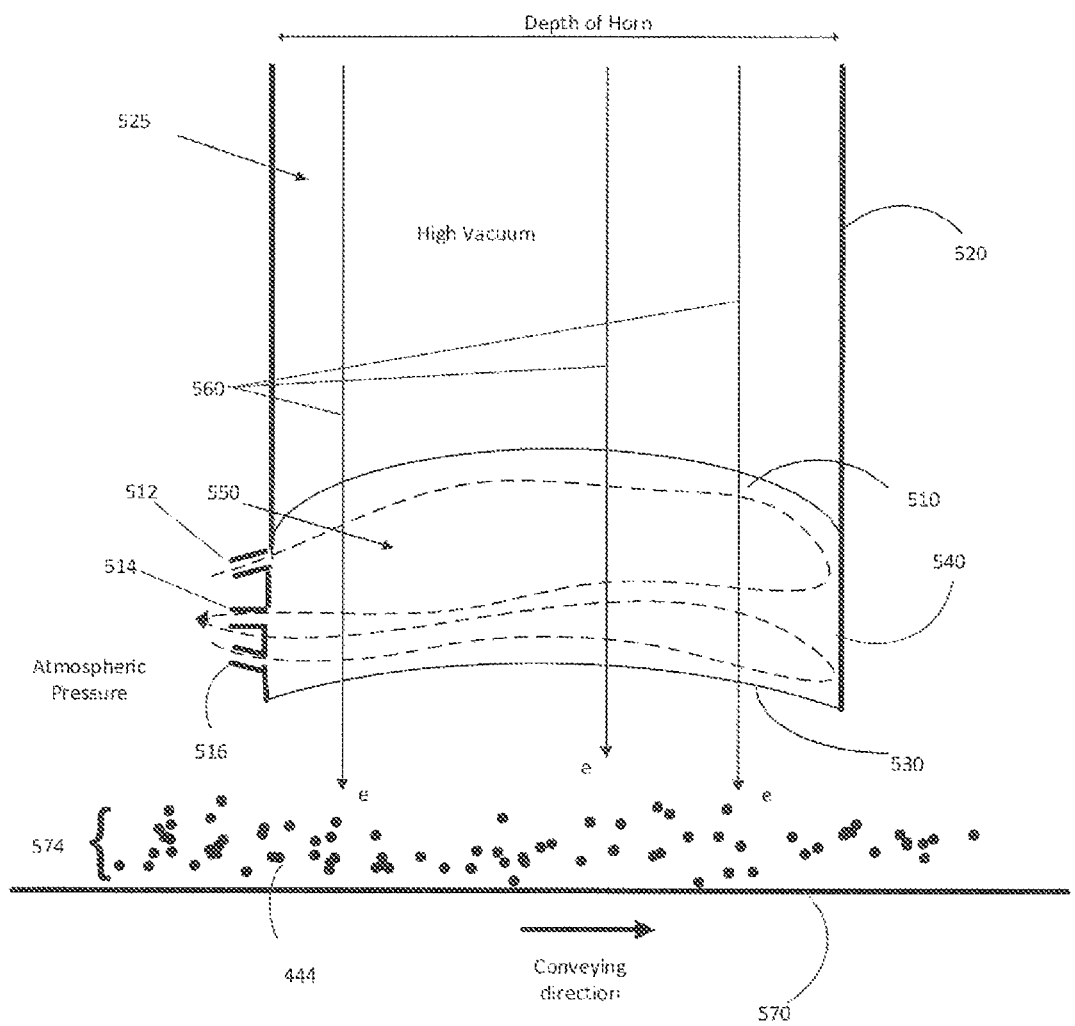
FIG. 5 is a cross section view through the depth of a scanning horn.

FIG. 5 is a cross sectional view of another embodiment of two foils window extraction system for a scanning electron beam. The primary foil window (510) in a scanning horn (520) is shown. The region indicated is a high vacuum area (525). Generally, the primary window is concave towards the high vacuum area (525). The secondary foil window (530) is flatter but is also concave in the same direction. This curvature helps provide structural support to the window and is mechanically stronger than a flat window. Alternatively the windows can be flat or curved in any direction. Sidewalls (540) and the primary and secondary windows can define an interior space (550). Since the primary and secondary windows are connected by sidewalls in this configuration both windows are part of the electron beam apparatus. Electrons (560) travel through both windows to impinge on and penetrate the biomass disposed beneath. A first inlet on one sidewall (512) is arranged to allow a cooling fluid (e.g., a liquid or a gas) to impinge on the primary window foil. The cooling fluid runs along the window and then reverses direction on meeting the far (opposite) wall and flows back generally through the center of the interior space as shown and then out through an exhaust port and or outlet (514). A second inlet (516) on the sidewall is arranged to allow cooling fluid to impinge on the secondary window foil in a similar fashion. Optionally more inlets (e.g., 2, 3, 4, 5, 6 or more) can bring cooling fluid to the primary and secondary window surfaces and more than one outlets (e.g., 2, 3, 4, 5, 6 or more) can allow the cooling fluid to exit the interior space. In some embodiments one or more side walls can even be a mesh, screen or grate with many openings through which cooling gas can flow while providing structural support to the windows. The system can include a conveyor, with a conveying surface (570). A material, for example biomass (444), can be conveyed in the direction indicated as a thin pile (574), e.g., about 0.25 inches. Electrons irradiated the material as it is conveyed under the two foil extraction system.

The Windows

The biomass is irradiated as it passes under a window, which is generally a metallic foil (e.g., titanium, titanium alloy, aluminum and/or silicon). The window is impermeable to gases, yet electrons can pass with low resistance. The foil windows are preferably between about 10 and 100 microns thick (e.g., about 10 microns thick to about 30 microns thick, about 15-40 microns, about 20-30 microns, about 5-30 microns, about 8-25 microns, about 10-20 microns, about 20-25 microns thick, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 microns thick). Thin windows are preferable to thick windows since thin windows dissipate less energy as an electron beam passes through them (e.g., the resistive heating is less since Power is the product of the square of the current and the resistance, $P=I^2R$). Thin windows are also less mechanically strong and more likely to fail which causes increased expense and more downtime for the equipment. The distance between the front surface of the primary window foil and back surface of the secondary window foil is preferably less than 30 cm, more preferably less than 20 cm, and most preferably less than 10 cm.

The foil window can be cooled by passing air or an inert gas over the window. When using an enclosure, it is generally preferred to mount the window to the enclosure and to cool the window from the side outside of the enclosed conveying system to avoid lofting up any particulates of the material being irradiated.

The system can include more than one window, e.g., a primary window and a secondary window. The two windows may form the enclosure to contain the purging gases and/or the cooling gases. The secondary window may serve a function as a "sacrificial" window, to protect the primary window. The electron beam apparatus includes a vacuum between the electron source and the primary window, and breakage of the primary window is likely to cause biomass material to be sucked up into the electron beam apparatus, resulting in damage, repair costs, and equipment downtime.

The window can be polymer, ceramic, coated ceramic, composite or coated composite. The secondary window can be, for instance, a continuous sheet/roll of polymer or coated polymer, which can be advanced continuously or at intervals to provide a clean or new section to serve as the secondary window.

The primary window and the secondary window can be made from the same material, or different materials. For instance, the primary window foil can be made from titanium, scandium, vanadium, chromium, nickel, zirconium, niobium, molybdenum, ruthenium, rhodium, palladium, hafnium, tantalum, tungsten, rhenium, platinum, iridium, or alloys or mixtures of any of these. The secondary single-type window foil can be made from titanium, scandium, vanadium, chromium, nickel, zirconium, niobium, molybdenum, ruthenium, rhodium, palladium, hafnium, tantalum, tungsten, rhenium, platinum, iridium, beryllium, aluminum, silicon, or alloys or mixtures of any of these. The primary and secondary windows can be of the same material, mixture of materials, or alloy, or different materials, mixtures of material or alloys. One or both of the windows can be laminates of the same of different materials, mixtures of materials, or alloys.

One of more of the windows can have a support structure across its face. The term "single-type window", as used herein, means a window with no support structure across its face. The term "double-type window", as used herein means a window with a support structure across its face, where the support structure effectively divides the surface of the window into two parts. Such a double-type window is shown in U.S. Pat. No. 5,877,582 to Nishimura. Additional support structures can also be used.

The primary window foil and the secondary window foil can both be made from low Z element. Alternatively, the primary window foil can be made from a high Z element, and the secondary window foil can be made from a low Z element.

The embodiments described herein do not preclude the inclusion of additional windows, which may have a protective function, or may be included to modify the radiation exposure.

The windows can be concave, flat or convex. It is generally preferred that the window be slightly convex, in a direction away from the direction of the cooling fluid. This curvature improves the mechanical strength of the window and increases the permitted temperature levels as well as allowing a better flow path for the cooling fluid. On the side of the scanning horn the curvature tends to be towards the vacuum (e.g., away from the cooling fluid) due to the vacuum (e.g., about $10^{-5}$ to $10^{-19}$ torr, about $10^{-6}$ to $10^{-9}$ torr, about $10^{-7}$ to $10^{-8}$ torr).

The cooling of the window and/or concave shape of the window become especially important for high beam currents, for example at least about 100 mA electron gun currents (e.g., at least about 110 mA, at least about 120 mA, at least about 130 mA, at least about 140 mA, at least about 150 mA at least about 200 mA, at least about 500 mA, at least about 1000 mA) because resistive heating is approximately related to the square of the current as discussed above. The windows can be any shape but typically are approximately rectangular with a high aspect ratio of the width to the length (where the width direction is the same as the width of the conveying system perpendicular to the conveying direction, and the length is the same as the direction of conveying). The distance of the window to the conveyed material can be less than about 10 cm (e.g., less than about 5 cm) and more than about 0.1 cm (e.g., more than about 1 cm, more than about 2 cm, more than about 3 cm, more than about 4 cm). It is also possible to use multiple windows (e.g., 3, 4, 5, 6 or more) with different and varied shapes and configured in different ways. For example, a primary or secondary foil window can include one, two or more windows in the same plane or layered and can include one or more support structures. For example, support structures can be a bar or a grid in the same plane and contacting the windows.

In some embodiments, the window that is mounted on the enclosed conveying system is a secondary foil window of a two foil window extraction system for a scanning electron beam. In other embodiments there is no enclosure for conveying the biomass material, e.g., the biomass is conveyed in air under the irradiation device.

Window Spacing

Although a large spacing between the windows can be advantageous, for example, for the reasons described above, the large spacing poses some disadvantages. One disadvantage of a large spacing between windows is that the electron beams will pass through a larger volume of cooling gas which can cause energy losses. For example, a 1 MeV beam loses about 0.2 MeV/m of energy, a 5 MeV beam loses about 0.23 MeV/m and a 10 MeV beam loses about 0.26 MeV/m. Therefore with a 1 MeV beam of electrons passing through 1 cm of air, the beam loses only 0.2% of its energy, at 10 cm of air, the beam loses 2% of its energy, at 20 cm this is 4% of its energy, while at 50 cm the energy loss is 10%. Since the electrons also have to travel from the secondary foil window to the biomass through additional air, the gap between the windows must be carefully controlled. Preferably, energy losses are less that about 20% (e.g., less than 10%, less than 5% or even less than 1%). It is therefore advantageous to minimize the spacing between the windows to decrease energy losses. Optimal spacing (e.g., average spacing) between the windows (e.g., between the surface side of the electron window foil and the facing surface of the secondary window foil) for the benefit of cooling as described above and for the benefit of reducing energy loss are less than 30 cm (e.g., between about 2 and 20 cm, between about 3 and 20 cm, between about 4 and 20 cm, between about 5 and 20 cm, between about 6 and 20 cm, between about 7 and 20 cm, between about 8 and 20 cm, between about 3 and 15 cm, between about 4 and 15 cm, between about 5 and 15 cm, between about 6 and 15 cm, between about 7 and 15 cm, between about 8 and 15 cm between about 3 and 10 cm, between about 4 and 10 cm, between about 5 and 10 cm, between about 6 and 10 cm, between about 7 and 10 cm, between about 8 and 10 cm, preferably less than 20 cm, and most preferably less than 10 cm.

Alternatively, at higher MeV equipment a greater gap can be tolerated. The higher gap can be as great as 75 cm. In some embodiments support structures for the windows can be used across the windows, although these types of structures are less preferred because of energy losses that can occur to the electron beam as it strikes these kinds of structures.

A large spacing between the windows can be advantageous because it defines a larger volume between the windows and allows for rapid flowing of a large volume cooling gasses for very efficient cooling. The inlets and outlets are between 1 mm and 120 mm in diameter (e.g., about 2 mm, about 5 mm about 10 mm, about 20 mm, about 50 mm or even about 100 mm). The cooling gas flow can be at between about 500-2500 CFM (e.g., about 600 to 2500 CFM, about 700-2500 CFM, about 800 to 2500 CFM, about 1000 to 2500 CFM, about 600 to 2000 CFM, about 700-2000 CFM, about 800 to 2000 CFM, about 1000 to 2000 CFM, about 600 to 1500 CFM, about 700-1500 CFM, about 800 to 1500 CFM, about 1000 to 1500 CFM). In some embodiments, about 50% of the gas is exchanged per about 60 seconds or less (e.g., in about 50 sec or less, in about 30 sec or less, in about 10 sec or less, in about 1 sec or less).

Cooling and Purging Gases

The cooling gas in the two foil window extraction system can be a purge gas or a mixture, for example air, or a pure gas. In some embodiments the gas is an inert gas such as nitrogen, argon, helium and or carbon dioxide. It is preferred to use a gas rather than a liquid since energy losses to the electron beam are minimized. Mixtures of pure gas can also be used, either pre-mixed or mixed in line prior to impinging on the windows or in the space between the windows. The cooling gas can be cooled, for example, by using a heat exchange system (e.g., a chiller) and/or by using boil off from a condensed gas (e.g., liquid nitrogen, liquid helium).

When using an enclosure, the enclosed conveyor can also be purged with an inert gas so as to maintain an atmosphere at a reduced oxygen level. Keeping oxygen levels low avoids the formation of ozone which in some instances is undesirable due to its reactive and toxic nature. For example, the oxygen can be less than about 20% (e.g., less than about 10%, less than about 1%, less than about 0.1%, less than about 0.01%, or even less than about 0.001% oxygen). Purging can be done with an inert gas including, but not limited to, nitrogen, argon, helium or carbon dioxide. This can be supplied, for example, from a boil off of a liquid source (e.g., liquid nitrogen or helium), generated or separated from air in situ, or supplied from tanks. The inert gas can be recirculated and any residual oxygen can be removed using a catalyst, such as a copper catalyst bed. Alternatively, combinations of purging, recirculating and oxygen removal can be done to keep the oxygen levels low.

The enclosure can also be purged with a reactive gas that can react with the biomass. This can be done before, during or after the irradiation process. The reactive gas can be, but is not limited to, nitrous oxide, ammonia, oxygen, ozone, hydrocarbons, aromatic compounds, amides, peroxides, azides, halides, oxyhalides, phosphides, phosphines, arsines, sulfides, thiols, boranes and/or hydrides. The reactive gas can be activated in the enclosure, e.g., by irradiation (e.g., electron beam, UV irradiation, microwave irradiation, heating, IR radiation), so that it reacts with the biomass. The biomass itself can be activated, for example by irradiation. Preferably the biomass is activated by the electron beam, to produce radicals which then react with the activated or unactivated reactive gas, e.g., by radical coupling or quenching.

Purging gases supplied to an enclosed conveyor can also be cooled, for example below about 25° C., below about 0° C., below about −40° C., below about −80° C., below about −120° C. For example, the gas can be boiled off from a compressed gas such as liquid nitrogen or sublimed from solid carbon dioxide. As an alternative example, the gas can be cooled by a chiller or part of or the entire conveyor can be cooled.

Beam Stops

In some embodiments the systems and methods include a beam stop (e.g., a shutter). For example, the beam stop can be used to quickly stop or reduce the irradiation of material without powering down the electron beam device. Alternatively the beam stop can be used while powering up the electron beam, e.g., the beam stop can stop the electron beam until a beam current of a desired level is achieved. The beam stop can be placed between the primary foil window and secondary foil window. For example, the beam stop can be mounted so that it is movable, that is, so that it can be moved into and out of the beam path. Even partial coverage of the beam can be used, for example, to control the dose of irradiation. The beam stop can be mounted to the floor, to a conveyor for the biomass, to a wall, to the radiation device (e.g., at the scan horn), or to any structural support. Preferably the beam stop is fixed in relation to the scan horn so that the beam can be effectively controlled by the beam stop. The beam stop can incorporate a hinge, a rail, wheels, slots, or other means allowing for its operation in moving into and out of the beam. The beam stop can be made of any material that will stop at least 5% of the electrons, e.g., at least 10%, 20%, 30%, 40%, 50%, 60%, 70%, at least 80%, 85%, 90%, 91%, 92%, 93%, 94%, 95%, 96%, 97%, 98%, 99% or even about 100% of the electrons. Useful levels of stopping electrons can be 10%, 20%, 40%, 60%, 80% and 96%

The beam stop can be made of a metal including, but not limited to, stainless steel, lead, iron, molybdenum, silver, gold, titanium, aluminum, tin, or alloys of these, or laminates (layered materials) made with such metals (e.g., metal-coated ceramic, metal-coated polymer, metal-coated composite, multilayered metal materials).

The beam stop can be cooled, for example, with a cooling fluid such as an aqueous solution or a gas. The beam stop can be partially or completely hollow, for example with cavities. Interior spaces of the beam stop can be used for cooling fluids and gases. The beam stop can be of any shape, including flat, curved, round, oval, square, rectangular, beveled and wedged shapes.

The beam stop can have perforations so as to allow some electrons through, thus controlling (e.g., reducing) the levels of radiation across the whole area of the window, or in specific regions of the window. The beam stop can be a mesh formed, for example, from fibers or wires. Multiple beam stops can be used, together or independently, to control the irradiation. The beam stop can be remotely controlled, e.g., by radio signal or hard wired to a motor for moving the beam into or out of position.

Radiation Sources

The type of radiation determines the kinds of radiation sources used as well as the radiation devices and associated equipment. The methods, systems and equipment described herein, for example for treating materials with radiation, can utilized sources as described herein as well as any other useful source.

Sources of gamma rays include radioactive nuclei, such as isotopes of cobalt, calcium, technicium, chromium, gallium, indium, iodine, iron, krypton, samarium, selenium, sodium, thalium, and xenon.

Sources of X-rays include electron beam collision with metal targets, such as tungsten or molybdenum or alloys, or compact light sources, such as those produced commercially by Lyncean.

Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

Sources for ultraviolet radiation include deuterium or cadmium lamps. Sources for infrared radiation include sapphire, zinc, or selenide window ceramic lamps. Sources for microwaves include klystrons, Slevin type RF sources, or atom beam sources that employ hydrogen, oxygen, or nitrogen gases.

Accelerators used to accelerate the particles (e.g., electrons or ions) can be electrostatic DC, e. g. electrodynamic DC, RF linear, magnetic induction linear or continuous wave. For example, various irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, Cockroft Walton accelerators (e.g., PELLETRON® accelerators), LINACS, Dynamitrons (e.g, DYNAMITRON® accelerators), cyclotrons, synchrotrons, betatrons, transformer-type accelerators, microtrons, plasma generators, cascade accelerators, and folded tandem accelerators. For example, cyclotron type accelerators are available from IBA, Belgium, such as the RHODOTRON™ system, while DC type accelerators are available from RDI, now IBA Industrial, such as the DYNAMITRON®. Other suitable accelerator systems include, for example: DC insulated core transformer (ICT) type systems, available from Nissin High Voltage, Japan; S-band LINACs, available from L3-PSD (USA), Linac Systems (France), Mevex (Canada), and Mitsubishi Heavy Industries (Japan); L-band LINACs, available from Iotron Industries (Canada); and ILU-based accelerators, available from Budker Laboratories (Russia). Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria. Some particle accelerators and their uses are disclosed, for example, in U.S. Pat. No. 7,931,784 to Medoff, the complete disclosure of which is incorporated herein by reference.

Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, which are then accelerated through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scanned magnetically in the x-y plane, where the electrons are initially accelerated in the z direction down the accelerator tube and extracted through a foil window. Scanning the electron beams is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of carbohydrate-containing materials, for example, by the mechanism of chain scission. In addition, electrons having energies of 0.5-10 MeV can penetrate low density materials, such as the biomass materials described herein, e.g., materials having a bulk density of less than 0.5 g/cm3, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially or built. For example elements or components such inductors, capacitors, casings, power sources, cables, wiring, voltage control systems, current control elements, insulating material, microcontrollers and cooling equipment can be purchased and assembled into a device. Optionally, a commercial device can be modified and/or adapted. For example, devices and components can be purchased from any of the commercial sources described herein including Ion Beam Applications (Louvain-la-Neuve, Belgium), NHV Corporation (Japan), the Titan Corporation (San Diego, Calif.), Vivirad High Voltage Corp (Billeric, Mass.) and/or Budker Laboratories (Russia). Typical electron energies can be 0.5 MeV, 1 MeV, 2 MeV, 4.5 MeV, 7.5 MeV, or 10 MeV. Typical electron beam irradiation device power can be 1 kW, 5 kW, 10 kW, 20 kW, 50 kW, 60 kW, 70 kW, 80 kW, 90 kW, 100 kW, 125 kW, 150 kW, 175 kW, 200 kW, 250 kW, 300 kW, 350 kW, 400 kW, 450 kW, 500 kW, 600 kW, 700 kW, 800 kW, 900 kW or even 1000 kW. Accelerators that can be used include NHV irradiators medium energy series EPS-500 (e.g., 500 kV accelerator voltage and 65, 100 or 150 mA beam current), EPS-800 (e.g., 800 kV accelerator voltage and 65 or 100 mA beam current), or EPS-1000 (e.g., 1000 kV accelerator voltage and 65 or 100 mA beam current). Also, accelerators from NHV's high energy series can be used such as EPS-1500 (e.g., 1500 kV accelerator voltage and 65 mA beam current), EPS-2000 (e.g., 2000 kV accelerator voltage and 50 mA beam current), EPS-3000 (e.g., 3000 kV accelerator voltage and 50 mA beam current) and EPS-5000 (e.g., 5000 and 30 mA beam current).

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments describe herein because of the larger scan width and reduced possibility of local heating and failure of the windows.

Subsequent Use of the Feedstocks

Using the methods described herein, a starting biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Biomass Material Preparation—Mechanical Treatments

The biomass can be in a dry form, for example with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-irradiation processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration, the desired biomass falls through the perforations or screen and thus biomass larger than the perforations or screen are not irradiated. These larger materials can be re-processed, for example by comminuting, or they can simply be removed from processing. In another configuration, material that is larger than the perforations is irradiated and the smaller material is removed by the screening process or recycled. In this kind of a configuration, the conveyor itself (for example a part of the conveyor) can be perforated or made with a mesh. For example, in one particular embodiment the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-processing can include heating the material. For example a portion of the conveyor can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-irradiation processing can include cooling the material. Cooling material is described in U.S. Pat. No. 7,900,857 to Medoff, the disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-irradiation processing can include adding a material to the biomass. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be treated as described herein, e.g. with electron beam radiation, while being conveyed. The biomass can be delivered to the conveyor by using, a belt conveyor, a pneumatic conveyor, a screw conveyor, a hopper, a pipe, manually or by combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils.

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through a treatment area, e.g., a radiation zone, optional post processing can be done. The optional post processing can, for example, be any process described herein. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of an enclosed conveyor and exposed to a gas (e.g., oxygen) where it is quenched, forming carboxylated groups. In one embodiment the biomass can be exposed during irradiation to a reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the carbohydrate-containing material. These processes can be applied before, during and or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the carbohydrate-containing material, increase the surface area of the carbohydrate-containing material and/or decrease one or more dimensions of the carbohydrate-containing material.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. For example, a feedstock material can be conveyed through ionizing radiation using a conveyor as described herein and then mechanically treated. Chemical treatment can remove some or all of the lignin (for example chemical pulping) and can partially or completely hydrolyze the material. The methods also can be used with pre-hydrolyzed material. The methods also can be used with material that has not been pre hydrolyzed. The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for opening up, stressing, breaking or shattering the carbohydrate-containing materials, making the cellulose of the materials more susceptible to chain scission and/or disruption of crystalline structure during the physical treatment.

Methods of mechanically treating the carbohydrate-containing material include, for example, milling or grinding. Milling may be performed using, for example, a hammer mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., 1/4- to 1/2-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source. The shredded fiber source. In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated carbohydrate-containing materials, are described in further detail in U.S. Pat. App. Pub. 2012/01000577 A1, filed Oct. 18, 2011, the full disclosure of which is hereby incorporated herein by reference.

Sonication, Pyrolysis, Oxidation, Steam Explosion

If desired, one or more sonication, pyrolysis, oxidative, or steam explosion processes can be used in addition to irradiation to further reduce the recalcitrance of the carbohydrate-containing material. These processes can be applied before, during and or after irradiation. These processes are described in detail in U.S. Pat. No. 7,932,065 to Medoff, the full disclosure of which is incorporated herein by reference.

Biomass Processing after Irradiation

After irradiation the biomass may be transferred to a vessel for saccharification. Alternately, the biomass can be heated after the biomass is irradiated prior to the saccharification step. The biomass can be, for example, by IR radiation, microwaves, combustion (e.g., gas, coal, oil, biomass), resistive heating and/or inductive coils. This heating can be in a liquid, for example, in water or other water-based solvents. The heat can be applied from at least one side or more than one side, can be continuous or periodic and can be for only a portion of the material or all the material. The biomass may be heated to temperatures above 90° C. in an aqueous liquid that may have an acid or a base present. For example, the aqueous biomass slurry may be heated to 90 to 150° C., alternatively, 105 to 145° C., optionally 110 to 140° C. or further optionally from 115 to 135° C. The time that the aqueous biomass mixture is held at the peak temperature is 1 to 12 hours, alternately, 1 to 6 hours, optionally 1 to 4 hours at the peak temperature. In some instances, the aqueous biomass mixture is acidic, and the pH is between 1 and 5, optionally 1 to 4, or alternately, 2 to 3. In other instances, the aqueous biomass mixture is alkaline and the pH is between 6 and 13, alternately, 8 to 12, or optionally, 8 to 11.

Saccharification

The treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/01000577 A1, filed Oct. 18, 2011.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the carbohydrate-containing material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the carbohydrate-containing material with the enzyme. The concentration can be controlled, e.g., by controlling how much saccharification takes place. For example, concentration can be increased by adding more carbohydrate-containing material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Sugars

In the processes described herein, for example after saccharification, sugars (e.g., glucose and xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example, glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts know in the art) in combination with $H_2$ under high pressure (e.g., 10 to 12000 psi). Other types of chemical transformation of the products from the processes described herein can be used, for example production of organic sugar derived products such (e.g., furfural and furfural-derived products). Chemical transformations of sugar derived products are described in U.S. Prov. App. No. 61/667,481, filed Jul. 3, 2012, the disclosure of which is incorporated herein by reference in its entirety.

Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption.

Additionally or alternatively, the fermentation products can be ground to a appropriate particle size by comminution.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

Fermentation includes the methods and products that are disclosed in U.S. Prov. App. No. 61/579,559, filed Dec. 22, 2012, and U.S. Prov. App. No. 61/579,576, filed Dec. 22, 2012, the contents of both of which are incorporated by reference herein in their entirety.

Mobile fermenters can be utilized, as described in International App. No. PCT/US2007/074028 (which was filed Jul. 20, 2007, was published in English as WO 2008/011598 and designated the United States), the contents of which is incorporated herein in its entirety. Similarly, the saccharification equipment can be mobile. Further, saccharification and/or fermentation may be performed in part or entirely during transit.

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts. Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

Other intermediates and products, including food and pharmaceutical products, are described in U.S. application Ser. No. 12/417,900 filed Apr. 3, 2009, the full disclosure of which is hereby incorporated by reference herein.

Carbohydrate Containing Materials (Biomass Materials)

As used herein, the term "biomass materials" is used interchangeably with the term "carbohydrate-containing materials", and includes lignocellulosic, cellulosic, starchy, and microbial materials. Any of the methods described herein can be practiced with mixtures of any biomass materials described herein.

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example paper products as described in U.S. application Ser. No. 13/396,365 ("Magazine Feedstocks" by Medoff et al., filed Feb. 14, 2012), the full disclosure of which is incorporated herein by reference.

Cellulosic materials can also include lignocellulosic materials which have been de-lignified.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femtoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 the full disclosure of which is incorporated herein by reference.

Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum*, and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei*, and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp.

(including, but not limited to, *C. thermocellum* (Philippidis, 1996, supra), *C. saccharobutylacetonicum, C. saccharobutylicum, C. Puniceum, C. beijernckii*, and *C. acetobutylicum*), *Moniliella pollinis, Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*.

Many such microbial strains are publicly available, either commercially or through depositories such as the ATCC (American Type Culture Collection, Manassas, Va., USA), the NRRL (Agricultural Research Sevice Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, RED STAR®/Lesaffre Ethanol Red (available from Red Star/ Lesaffre, USA), FALI® (available from Fleischmann's Yeast, a division of Burns Philip Food Inc., USA), SUPER-START® (Lallemand Biofuels and Distilled Spirits, Canada), EAGLE C6 FUEL™ or C6 FUEL™ (available from Lallemand Biofuels and Distilled Spirits, Canada), GERT STRAND® (available from Gert Strand AB, Sweden) and FERMOL® (available from DSM Specialties).

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points. When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A system for cooling multiple single-type window foils of an electron beam accelerator comprising:
    a primary single-type window foil communicating with a vacuum side of a scanning horn of the electron beam accelerator;
    a secondary single-type window foil positioned on an atmospheric side of the scanning horn, wherein the distance of the secondary window to a biomass material under irradiation is more than 0.1 cm and less than 10 cm;
    a first flow path for providing a first cooling gas across the primary single-type window foil and second flow path for providing a second cooling gas across the secondary single-type window foil, the secondary single-type window foil being exposed to atmospheric pressure;
    a pivoting beam stop configured to pivot between the primary single-type window and the secondary single-type window to block an electron beam of the accelerator;
    a conveyor that is configured to move the biomass material through an irradiation zone under the secondary single-type window foil;
    wherein the primary and secondary single-type window foils are positioned with a gap of less than about 9 cm between them.

2. The system of claim 1, wherein the window foils are metallic.

3. The system of claim 2, wherein both the primary single-type window foil and the secondary single-type window foil are part of the scanning horn of the electron beam accelerator, where
    at least one inlet is provided and which allows a cooling gas to enter the gap defined between the primary and the secondary single-type window foils and
    at least one outlet is provided to extract cooling gases from the gap defined between the primary and secondary single-type window foils.

4. The system of claim 3, further including a cooling chamber, the cooling chamber including four walls and the interior volume is approximately rectangular prism in shape.

5. The system of claim 2, further including a treatment enclosure with a cover surface, where the enclosure is positioned on a side of the secondary single-type window foil opposite the electron beam accelerator and the conveyor is within the treatment enclosure.

6. The system of claim 5, wherein the secondary single-type window foil is mounted on the cover surface and is integral to the treatment enclosure.

7. The system of claim 6, wherein the cover surface is perpendicular to the electron beam accelerator.

8. The system of claim 7, wherein the treatment enclosure has a first opening.

9. The system of claim 8, wherein the conveyor is configured to move the biomass material through the first opening prior to moving the biomass material under the secondary single-type window.

10. The system of claim 9, wherein the treatment enclosure includes a second opening.

11. The system of claim 10, wherein the conveyor further provides for moving the treated biomass material out of the treatment enclosure through the second opening.

12. The system of claim 11, further providing for purging the treatment enclosure with an inert gas.

13. The system of claim 1, wherein the primary single-type window foil is made from an element selected from the group consisting of: titanium, scandium, vanadium, chromium, nickel, zirconium, niobium, molybdenum, ruthenium, rhodium, palladium, hafnium, tantalum, tungsten, rhenium, platinum, iridium, and alloys or mixtures of any of these.

14. The system of claim 1, wherein the secondary single-type window foil is made from an element selected from the group consisting of: titanium, scandium, vanadium, chromium, nickel, zirconium, niobium, molybdenum, ruthenium, rhodium, palladium, hafnium, tantalum, tungsten, rhenium, platinum, iridium, beryllium, aluminum, silicon, and alloys or mixtures of any of these.

15. The system of claim 1, wherein the primary single-type window foil is from 10 to 50 microns thick.

16. The system of claim 15, wherein the primary single-type window foil is from 15 to 40 microns thick.

17. The system of claim 15, wherein the primary single-type window foil is from 20 to 30 microns thick.

18. The system of claim 15, wherein the secondary single-type window foil is from 5 to 30 microns thick.

19. The system of claim 15, wherein the secondary single-type window foil is from 8 to 25 microns thick.

20. The system of claim 15, wherein the secondary single-type window foil is from 10 to 20 microns thick.

21. The system of claim 9, wherein the biomass material is selected from the group consisting of: cellulosic material, lignocellulosic material, and starchy material.

22. The system of claim 9, wherein the biomass material is selected from the group consisting of paper, paper products, paper waste, wood, particle board, sawdust, agricultural waste, sewage, silage, grasses, wheat straw, rice hulls, bagasse, cotton, jute, hemp, flax, bamboo, sisal, abaca, straw, corn cobs, corn stover, alfalfa, hay, coconut hair, seaweed, algae, and mixtures thereof.

23. The system of claim 9, wherein the biomass material is treated with between 10 and 200 Mrad of radiation.

24. The system of claim 9, wherein the biomass material is treated with between 10 and 75 Mrad of radiation.

25. The system of claim 9, wherein the biomass material is treated with between 15 and 50 Mrad of radiation.

26. The system of claim 9, wherein the biomass material is treated with between 20 and 35 Mrad of radiation.

27. The system of claim 2, wherein the electron beam accelerator includes electrons having an energy of about 0.5-10 MeV.

28. The system of claim 2, wherein the electron beam accelerator includes electrons having an energy of about 0.8-5 MeV.

29. The system of claim 2, wherein the electron beam accelerator includes electrons having an energy of about 0.8-3 MeV.

30. The system of claim 2, wherein the electron beam accelerator includes electrons having an energy of about 1-3 MeV.

31. The system of claim 2, wherein the electron beam accelerator includes electrons having an energy of about 1 MeV.

32. The system of claim 2, wherein the electron beam accelerator includes a beam current of at least about 50 mA.

33. The system of claim 2, wherein the electron beam accelerator includes a beam current of at least about 60 mA.

34. The system of claim 2, wherein the electron beam accelerator includes a beam current of at least about 70 mA.

35. The system of claim 2, wherein the electron beam accelerator includes a beam current of at least about 80 mA.

36. The system of claim 2, wherein the electron beam accelerator includes a beam current of at least about 90 mA.

37. The system of claim 2, wherein the electron beam accelerator includes a beam current of at least about 100 mA.

38. The system of claim 2, wherein the electron beam accelerator includes a beam current of at least about 125 mA.

39. The system of claim 2, wherein the electron beam accelerator includes a beam current of at least about 150 mA.

40. The system of claim 1, wherein the beam stop is moveable to absorb different amounts of the electron beam.

41. The system of claim 1, wherein the beam stop absorbs at least 20% of incident electrons.

42. The system of claim 1, wherein the beam stop absorbs at least 40% of incident electrons.

43. The system of claim 1, wherein the beam stop absorbs at least 60% of incident electrons.

44. The system of claim 1, wherein the beam stop absorbs at least 80% of incident electrons.

45. The system of claim 1, wherein the conveyor is configured to move the biomass material through the irradiation zone which is at atmospheric pressure.

* * * * *